US008252807B2

(12) United States Patent
Logsdon et al.

(10) Patent No.: US 8,252,807 B2
(45) Date of Patent: Aug. 28, 2012

(54) METHODS OF INHIBITING THE INTERACTION BETWEEN S100 AND THE RECEPTOR FOR ADVANCED GLYCATION END-PRODUCTS

(75) Inventors: Craig D. Logsdon, Houston, TX (US); William Bornmann, Missouri City, TX (US)

(73) Assignee: Board of Regents, The University of Texas System

( * ) Notice: Subject to any disclaimer, the term of this patent is extended or adjusted under 35 U.S.C. 154(b) by 476 days.

(21) Appl. No.: 12/247,635

(22) Filed: Oct. 8, 2008

(65) Prior Publication Data
US 2009/0062319 A1 Mar. 5, 2009

Related U.S. Application Data

(63) Continuation-in-part of application No. 12/041,112, filed on Mar. 3, 2008.

(60) Provisional application No. 60/892,652, filed on Mar. 2, 2007.

(51) Int. Cl.
*A61K 31/353* (2006.01)
*A61K 31/513* (2006.01)
(52) U.S. Cl. ...................................... 514/274; 514/456
(58) Field of Classification Search .................. 514/274, 514/456
See application file for complete search history.

(56) References Cited

U.S. PATENT DOCUMENTS
2005/0009067 A1* 1/2005 Logsdon et al. ................. 435/6

FOREIGN PATENT DOCUMENTS
EP          0 413 583    * 8/1990
WO     WO2005/021722    * 3/2005

OTHER PUBLICATIONS

Morissette et al. High-throughput crystallization: polymorphs, salts, co-crystals and solvates of pharmaceutical solids. Adv. Drug Del. Rev. 56 (2004), 275-300.*
Vippagunta et al. Crystalline solids. Adv. Drug. Del. Rev. 48 (2001), 3-26.*
Arumugam et al. Effect of Cromolyn on S100P Interactions With RAGE and Pancreatic Cancer Growth and Invasion in Mouse Models. J. Nat. Canc. Inst. 98(24), 1806-1818 (2006).*
PubMed Health Fact Sheet: cromolyn sodium (intal) (2010). Accessed online at http://www.ncbi.nlm.nih.gov/pubmedhealth/PMH0000042/ on Jun. 9, 2011.*
Jemal, A., Murray, T., Samuels, A., Ghafoor, A., Ward, E., and Thun, M.J., "CA A Cancer Journal for Clinicians," Cancer Statistics, Jan. 2003; vol. 53 No. 1, pp. 5-26.
Maheshwari, V., Moser, A.J. "Current management of locally advanced pancreatic cancer," Nature Clinical Practice Gastroenterology & Hepatology; Aug. 2005; vol. 2 No. 8, pp. 356-364.

Ko, A. H. and Tempero, M. A. "Treatment of Metastatic Pancreatic Cancer," Journal of the National Comprehensive Cancer Network, Sep. 2005; vol. 3 No. 5, pp. 627-636.
Moore, M.J., Hamm, J., Dancey, J., Eisenberg, P.D., Dagenais, M., Fields, A., et al. "Comparison of Gemcitabine Versus the Matrix Metalloproteinase Inhibitor BAY 12-9566 in Patients with Advanced or Metastatic Adenocarcinoma of the Pancreas: A Phase III Trial of the National Cancer Institute of Canada Clinical Trials Group," Journal of Clinical Oncology, Sep. 1, 2003, vol. 21, No. 17, pp. 3296-3302.
Logsdon, C.D., Simeone, D.M., Binkley, C., Arumugam, T., Greenson, J.K., Giordano, T.J., et al. "Molecular Profiling of Pancreatic Adenocarcinoma and Chronic Pancreatitis Identifies Multiple Genes Differentially Regulated in Pancreatic Cancer." Cancer Research, May 15, 2003; vol. 63 No. 10, pp. 2649-2657.
Crnogorac-Jurcevic, T., Missiaglia, E., Blaveri, E., Gangeswaran, R., Jones, M., Terris, B., et al. "Molecular Alterations in pancreatic carcinoma: expression profiling shows that dysregulated expression of S100 genes is highly prevalent," J Pathol 2003, July, vol. 201, No. 1, pp. 63-74.
Sato, N., Fukushima, N., Matsubayashi, H., Goggins, M. "Identification of maspin and S100P as novel hypomethylation targets in pancreatic cancer using global gene expression profiling." Oncogene, Feb. 26, 2004, vol. 23, No. 8, pp. 1531-1538.
Wang, G.Z., Platt-Higgins, A., Carroll, J., Rudland, S.D., Winstanley, J., Barraclough, R., et al. "Induction of Metastasis by S100P in a Rat Mammary Model and Its Association with Poor Survival of Breast Cancer Patients." Cancer Research, Jan. 15, 2006, vol. 66, No. 2, pp. 1199-1207.
Beer, D.G., Kardia, S.L., Huang, C.C., Giordano, T.J., Levin, A.M., Misek, D.E., et al. "Gene-expression profiles predict survival of patients with lung adenocarcinoma." Nature Medicine, Aug. 2002, vol. 8, No. 8, pp. 816-824.
Becker, T., Gerke, V., Kube, E., Weber, K. "S100P, a novel Ca(2+)-binding protein from human placenta. cDNA cloning, recombinant protein expression and Ca(2+) binding properties." Eur. J. Biochem, Jul. 15, 1992, vol. 207No. 2, pp. 541-547.
Arumugam, T., Simeone, D.M., Van Golen, K., Logsdon, C.D. "S100P Promotes Pancreatic Cancer Growth, Survival, and Invasion," Clin Cancer Res Aug. 1, 2005, vol. 11, No. 15, pp. 5356-5364.
Bertram J, Palfner K, Hiddemann W, Kneba M. Elevated expression of S100P, CAPL and MAGE 3 in doxorubicin-resistant cell lines: comparison of mRNA differential display reverse transcription-polymerase chain reaction and subtractive suppressive hybridization for the analysis of differential gene expression. Anticancer Drugs Apr. 1998;9 (4):311-7.
Arumugam T, Simeone DM, Schmidt AM, Logsdon CD. S100P stimulates cell proliferation and survival via receptor for activated glycation end products (RAGE). J Biol Chem Feb. 13, 2004;279(7):5059-65.

(Continued)

Primary Examiner — Barbara P Badio
Assistant Examiner — Sara E Townsley
(74) Attorney, Agent, or Firm — Nielsen IP Law LLC.

(57) ABSTRACT

A method of inhibiting an interaction between a S100 protein and the receptor for advanced glycation end-products is provided comprising administering to a subject a therapeutically effective amount of cromolyn, C5, or salt, hydrate, or solvate thereof. In some embodiments, the S100 protein is S100P. In some embodiments, the S100 protein is S100P. In addition, the present invention provides a method of treating a cancer comprising administering to a mammal a therapeutically effective amount of cromolyn, C5, or salt, hydrate, or solvate thereof. Additional methods are also provided.

5 Claims, 22 Drawing Sheets

OTHER PUBLICATIONS

Stern D, Du YS, Fang YS, Marie SA. Receptor for advanced glycation endproducts: a multiligand receptor magnifying cell stress in diverse pathologic settings. Adv Drug Deliv Rev Dec. 7, 2002;54(12):1615-25.

Wang W, Abbruzzese JL, Evans DB, Larry L, Cleary KR, Chiao PJ. The nuclear factor-kappa B RelA transcription factor is constitutively activated in human pancreatic adenocarcinoma cells. Clin Cancer Res Jan. 1999;5(1):119-27.

Karin M, Cao Y, Greten FR, Li ZW. NF-kappaB in cancer: from innocent bystander to major culprit. Nat Rev Cancer Apr. 2002;2(4):301-10.

Arlt A, Vorndamm J, Breitenbroich M, Folsch UR, Kalthoff H, Schmidt WE, et al. Inhibition of NF-kappaB sensitizes human pancreatic carcinoma cells to apoptosis induced by etoposide (VP16) or doxorubicin. Oncogene Feb. 15, 2001;20(7):859-68.

Storms W, Kaliner MA. Cromolyn sodium: fitting an old friend into current asthma treatment. J Asthma Mar. 2005;42 (2):79-89.

Oyama Y, Shishibori T, Yamashita K, Naya T, Nakagiri S, Maeta H, et al. Two distinct anti-allergic drugs, amlexanox and cromolyn, bind to the same kinds of calcium binding proteins, except calmodulin, in bovine lung extract. Biochem Biophys Res Commun Nov. 17, 1997;240(2):341-7.

Okada M, Tokumitsu H, Kubota Y, Kobayashi R. Interaction of S100 proteins with the antiallergic drugs, olopatadine, amlexanox, and cromolyn: Identification of putative drug binding sites on S100A1 protein. Biochem Biophys Res Commun Apr. 12, 2002;292(4):1023-30.

Shishibori T, Oyama Y, Matsushita O, Yamashita K, Furuichi H, Okabe A, et al. Three distinct anti-allergic drugs, amlexanox, cromolyn and tranilast, bind to S100A12 and S100A13 of the S100 protein family. Biochem J Mar. 15, 1999;338 ( Pt 3):583-9.

Peiper M, Nagoshi M, Patel D, Fletcher JA, Goegebuure PS, Eberlein TJ. Human pancreatic cancer cells (MPanc-96) recognized by autologous tumor-infiltrating lymphocytes after in vitro as well as in vivo tumor expansion. Int J Cancer Jun. 11, 1997;71(6):993-9.

Qin XF, An DS, Chen IS, Baltimore D. Inhibiting HIV-1 infection in human T cells by lentiviral-mediated delivery of small interfering RNA against CCR5. Proc Natl Acad Sci U S A Jan. 7, 2003;100(1):183-8.

Mazurek N, Schindler H, Schurholz T, Pecht I. The cromolyn binding protein constitutes the Ca2+ channel of basophils opening upon immunological stimulus. Proc Natl Acad Sci U S A Nov. 1984;81(21):6841-5.

Cox A, Law NM, Findlay JB. Inhibition of cromolyn-induced phosphorylation of a 78-kDa protein by phorbol esters in rat peritoneal mast cells. Biochem Pharmacol Mar. 1, 1998;55(5):585-94.

Garland LG, Mongar JL. Inhibition by cromoglycate of histamine release from rat peritoneal mast cells induced by mixtures of dextran, phosphatidyl serine and calcium ions. Br J Pharmacol Jan. 1974;50(1):137-43.

White JR, Pearce FL. Effect of anti-allergic compounds on anaphylactic histamine secretion from rat peritoneal mast cells in the presence and absence of exogenous calcium. Immunology Jun. 1982;46(2):361-7.

Holian A, Hamilton R, Scheule RK. Mechanistic aspects of cromolyn sodium action on the alveolar macrophage: inhibition of stimulation by soluble agonists. Agents Actions Jul. 1991;33(3-4):318-25.

Correia I, Wang L, Pang X, Theoharides TC. Characterization of the 78 kDa mast cell protein phosphorylated by the antiallergic drug cromolyn and homology to moesin. Biochem Pharmacol Aug. 9, 1996;52(3):413-24.

Reinsprecht M, Pecht I, Schindler H, Romanin C. Potent block of Cl-channels by antiallergic drugs. Biochem Biophys Res Commun Nov. 16, 1992;188(3):957-63.

Lucas AM, Shuster S. Cromolyn inhibition of protein kinase C activity. Biochem Pharmacol Feb. 15, 1987;36(4):562-5.

Hemmerich S, Yarden Y, Pecht I. A cromoglycate binding protein from rat mast cells of a leukemia line is a nucleoside diphosphate kinase. Biochemistry May 19, 1992;31(19):4574-9.

Samoszuk M, Corwin MA. Mast cell inhibitor cromolyn increases blood clotting and hypoxia in murine breast cancer. International Journal of Cancer Oct. 20, 2003;107(1):159-63.

Ionov ID. Inhibition of Mast-Cell Activity As a New Approach to Anticancer Therapy. International Journal of Radiation Biology Jul. 1991;60(1-2):287-91.

Donato R. Intracellular and extracellular roles of S100 proteins. Microsc Res Tech Apr. 15, 2003;60(6):540-51.

Averboukh L, Liang P, Kantoff PW, Pardee AB. Regulation of S100P expression by androgen. Prostate Dec. 1996;29 (6):350-5.

Crnogorac-Jurcevic T, Efthimiou E, Nielsen T, Loader J, Terris B, Stamp G, et al. Expression profiling of microdissected pancreatic adenocarcinomas. Oncogene Jul. 4, 2002;21(29):4587-94.

Cairns H, Fitzmaurice C, Hunter D, Johnson PB, King J, Lee TB, Lord GH, Minshull R, Cox JS., Synthesis and structure-activity relationships of disodium cromoglycate and some related compounds. J Med Chem. Jun. 1972; 15 (6):583-9.

* cited by examiner

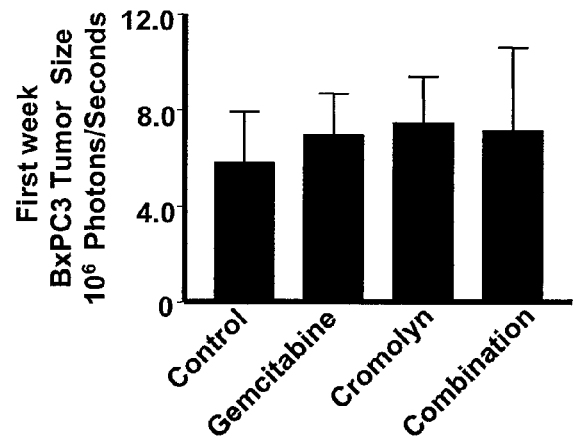
FIG. 4A
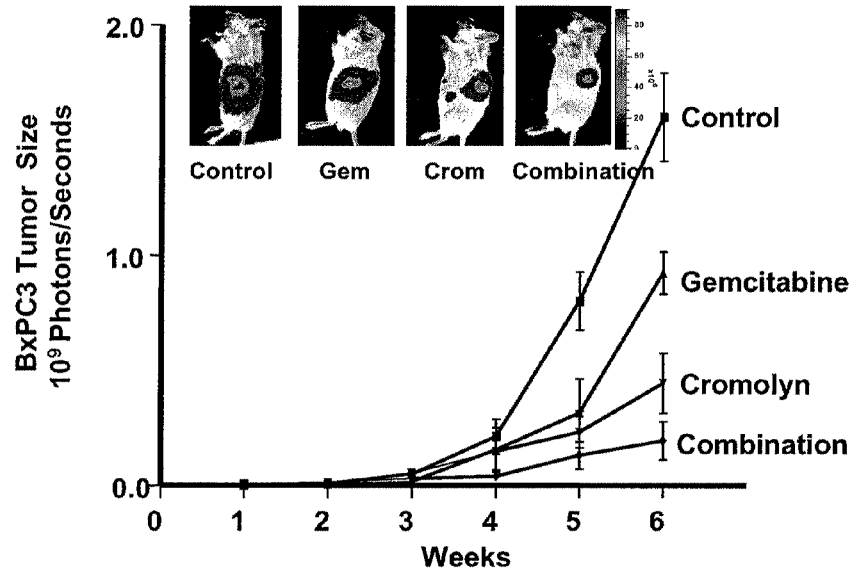
FIG. 4B
FIG. 4C
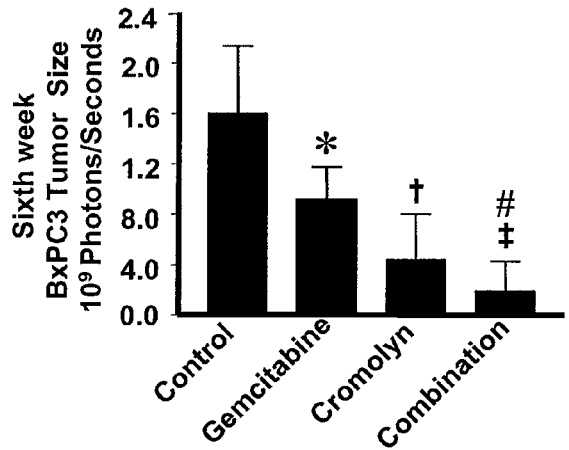

METHODS OF INHIBITING THE INTERACTION BETWEEN S100 AND THE RECEPTOR FOR ADVANCED GLYCATION END-PRODUCTS

CROSS-REFERENCE TO RELATED APPLICATION

The present application is a continuation-in-part of U.S. patent application Ser. No. 12/041,112, filed Mar. 3, 2008, which claims priority to commonly owned U.S. Provisional Patent Application Ser. No. 60/892,652; filed Mar. 2, 2007, both of which are incorporated by reference herein for all purposes.

BACKGROUND

The present disclosure, according to specific example embodiments, generally relates to methods of inhibiting the interaction between a S100 molecule and the receptor for advanced glycation end-products (RAGE). In particular, the present disclosure relates to inhibiting the interaction between a S100 molecule and RAGE using cromolyn compounds and/or a C5 compound.

Despite recent advances in understanding the biology of pancreatic cancer and molecular alterations in tumor pathogenesis, pancreatic cancer remains an oncologic challenge, with a 5-year survival rate of less than 5%. Pancreatic adenocarcinoma is arguably the most lethal of all cancers, with more than 95% of patients diagnosed with the disease dying from it, more than half within 6 months. In the United States, it ranks fourth among the leading causes of cancer death, accounting for more than 30,000 deaths annually. There is no effective therapy for pancreatic cancer other than early resection, but only a small percentage of patients are good candidates for surgery. Gemcitabine is the current conventional chemotherapy for pancreatic cancer, and it provides meager benefits. Combinations of gemcitabine with radiation or with other cytotoxic agents have also proven disappointing.

Because of the poor response to these standard forms of therapy, recent efforts have focused on the application of novel, biologically targeted agents aimed at well-known cancer mechanisms. Examples of these approaches include compounds that target vascular endothelial growth factor receptors, e.g., bevacizumab; the epidermal growth factor (EGF) receptor, e.g., cetuximab; the EGFR-activating tyrosine kinase, e.g., erlotinib and gefitinib; and K-ras e.g., farnesyol transferase inhibitor tipifarnib. However, most clinical trials with these agents have shown only a very modest survival advantage when compared to standard gemcitabine treatment.

SUMMARY

Methods of inhibiting the interaction between a S100 molecule and the receptor for advanced glycation end-products (RAGE) are disclosed. In particular, methods of inhibiting the interaction between a S100 molecule and RAGE using cromolyn compounds and/or a C5 compound are provided.

Methods of inhibiting an interaction between a S100 protein and the receptor for advanced glycation end-products comprise the step of administering to a subject in need thereof a therapeutically effective amount of a compound represented by the following Formula (I) or salt, hydrate, or solvate thereof:

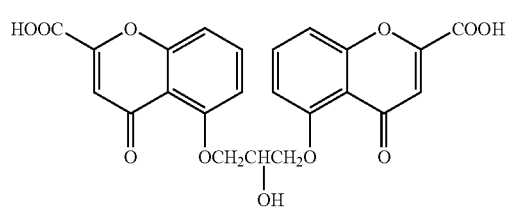

Formula (I)

Methods of inhibiting an interaction between a S100 protein and the receptor for advanced glycation end-products are provided that comprise the step of administering to a subject a therapeutically effective amount of a compound represented by the following Formula (II) or salt, hydrate, or solvate thereof:

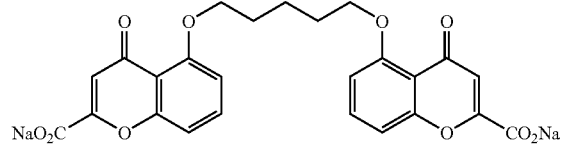

Formula (II)

Methods of treating a cancer are also provided comprising the step of administering to a mammal a therapeutically effective amount of a compound represented by the following Formula (II) or salt, hydrate, or solvate thereof:

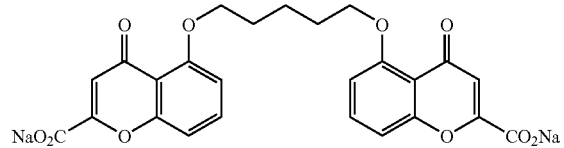

Formula (II)

The features and advantages of the methods and compounds provided herein will be readily apparent to those skilled in the art. While numerous changes may be made by those skilled in the art, such changes are within the spirit of the invention.

BRIEF DESCRIPTION OF DRAWINGS

Some specific example embodiments of the disclosure may be understood by referring, in part, to the following description and the accompanying drawings.

FIG. 2A shows Panc-1 cell invasion in the presence of 100 nM S100P with (+) or without (−) cromolyn (100 μM), and cell invasion after 24 hours. *, P<0.001 versus control, #, P<0.001 versus S100P (n=3). FIG. 2B shows photographs of representative membranes from experiments in FIG. 2A, after Diff-Quick staining. FIG. 2C shows BxPC-3 cell invasion in the presence of cromolyn (0 μM, 1 μM, 10 μM, and 100 μM) after 24 hours. *, P=0.008, †, P<0.001 versus control. FIG. 2D shows photographs of representative membranes from experiments in FIG. 2C, after Diff-Quick staining. Data are expressed as the percent invasion through the matrigel matrix and membrane relative to migration through the control membrane. Means and 95% confidence intervals from three independent experiments performed in triplicate are shown. Two-tailed two-sample (unpaired) Student's t-tests were used to determine P values.

FIG. 3A shows Panc-1 cells were plated at $5.0 \times 10^3$ cells/well, treated for 5 hours with 0 nM, 1 nM, 10 nM and 100 nM of S100P, with or without cromolyn (100 EM), and activity of a luciferase gene driven by the NFκB promoter was analyzed. Means and 95% confidence intervals are shown for three independent experiments performed in triplicate. *, P=0.022, †, P<0.001, and ‡, P<0.001 versus control; #, P=0.005 versus 100 nM S100P alone. FIG. 3B shows BxPC-3 cells were plated at $5.0 \times 10^3$ cells/well and treated for 5 hours with 0 μM, 1 μM, 10 μM, and 100 μM of cromolyn, and NFκB reporter luciferase activity was analyzed. Means and 95% confidence intervals are shown for three independent experiments performed in triplicate. *, P=0.003, †, P<0.001 versus control. FIG. 3C shows BxPC-3 cells stably expressing the NFκB reporter construct were transplanted orthotopically into the pancreas of nude mice. After 1 week, tumor growth was assessed and NFκB activity was analyzed using an IVIS system (Xenogen Corp., Alameda, Calif.) after injecting mice with D-luciferin (150 mg per kg body weight) (0 time point). The mice were treated with cromolyn (5 mg per kg body weight by intraperitoneal injection), and NFκB luciferase activity was analyzed again at 24 and 48 hours. *, P=0.005 versus control. Means and 95% confidence intervals are shown for two independent experiments (n=4 mice per group). Two-tailed two-sample (unpaired for in vitro and paired for in vivo studies) Student's t-tests were used to determine P values.

FIGS. 4A-4F show the effect of cromolyn on BxPC-3 tumor growth and metastasis in vivo. BxPC-3 cells stably expressing the firefly luciferase gene were injected orthotopically into 4 week old male CB 17 scid mice. FIG. 4A shows the estimated tumor volume after 1 week, obtained by using bioluminescence imaging. Mice were divided into four groups of five mice each with an equivalent mean tumor size between groups. FIG. 4B shows the estimated tumor volume each week for six weeks, using bioluminescence imaging. One group was treated with water (control), one group received gemcitabine bi-weekly (125 mg kg body weight bi-weekly by intraperitoneal injection), one group was administered cromolyn daily (5 mg per kg body weight daily by intraperitoneal injection), and the final group was given the combination of daily cromolyn and bi-weekly gemcitabine. All groups were treated for six weeks. Bioluminescent imaging was done weekly to assess tumor growth. FIG. 4C shows the volumes of primary tumors at the end of six weeks. *, P=0.013; †, P=0.001; ‡, P<0.001 versus control, #, P<0.001 versus gemcitabine. FIG. 4D shows the assessment of metastasis to the liver after the removal of the primary tumor. *, P=0.04 versus control. FIG. 4E shows the assessment of metastasis to the lung after the removal of the primary tumor. *, P=0.01; †, P=0.01 versus control, #, P=0.01 versus gemcitabine. FIG. 4F shows the weight of the mice at the end of experiment. *, P=0.013; †, P=0.022 versus control. Means and 95% confidence intervals are shown. (n=20). Two-tailed two-sample (unpaired) Student's t-tests were used to determine P values.

FIG. 5A shows the estimated tumor volume after 1 week, obtained by using bioluminescence imaging. Mice were divided into four groups of five mice each with an equivalent mean tumor size between groups. FIG. 5B shows the estimated tumor volume each week for six weeks, using bioluminescence imaging. One group was treated with water (control), one group received gemcitabine bi-weekly (125 mg per kg body weight bi-weekly by intraperitoneal injection), one group was administered cromolyn daily (5 mg per kg body weight daily by intraperitoneal injection), and the final group was given the combination of cromolyn and gemcitabine. All groups were treated for six weeks. Bioluminescent imaging was done weekly to assess tumor growth. FIG. 5C shows the volumes of primary tumors at the end of six weeks. *, P<0.001; †, P=0.009; ‡, P<0.001 versus control, #, P=0.02 versus gemcitabine. FIG. 5D shows the assessment of metastasis to the liver after the removal of the primary tumor. *, P=0.014; †, P=0.017; ‡, P=0.001 versus control. FIG. 5E shows the assessment of metastasis to the lung after the removal of the primary tumor. *, P=0.03; †, P=0.013; ‡, P=0.012 versus control. FIG. 5F shows the weight of the mice at the end of experiment. Means and 95% confidence intervals from two independent experiments are shown (n=20). Two-tailed two-sample (unpaired) Student's t-tests were used to determine P values.

FIG. 6A shows the estimated tumor volume after 1 week, obtained by using bioluminescence imaging. Mice were divided into four groups of five mice each with an equivalent mean tumor size between groups. FIG. 6B shows the estimated tumor volume each week for six weeks, using bioluminescence imaging. One group was treated with water (control), one group received gemcitabine bi-weekly (125 mg per kg body weight bi-weekly by intraperitoneal injection), one group was administered cromolyn daily (5 mg per kg body weight daily by intraperitoneal injection), and the final group was given the combination of cromolyn and gemcitabine. All groups were treated for six weeks. Bioluminescent imaging was done weekly to assess tumor growth. FIG. 6C shows the volumes of primary tumors at the end of six weeks. FIG. 6D shows the assessment of metastasis to the liver after the removal of the primary tumor. FIG. 6E shows the assessment of metastasis to the lung after the removal of the primary tumor. FIG. 6F shows the weight of the mice at the end of experiment. *, P=0.024 versus control. Means and 95% confidence intervals from two independent experiments are shown (n=20). Two-tailed two-sample (unpaired) Student's t-tests were used to determine P values.

FIG. 17 shows SW480 cell invasion in the presence of cromolyn (0 μM, 10 μM, and 100 μM) after 24 hours. *, P<0.05.

Figure 1A:
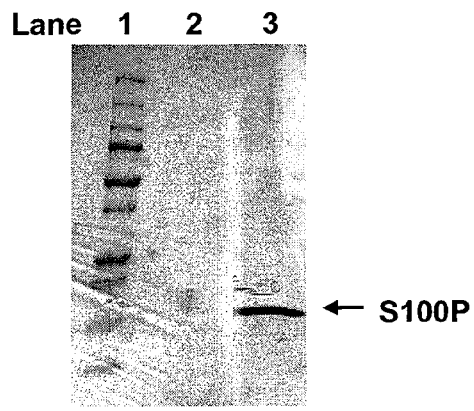
FIG. 1A shows the effect of cromolyn on the interaction of S100P with RAGE and cancer cell growth, survival, and invasiveness in vitro. Cromolyn was coupled with the amino group of AF-amino TOYOPEARL to generate a cromolyn affinity column. A negative control column was prepared by blocking the amino group. Purified S100P was added to both columns, which were then washed extensively. Protein was eluted from the columns using EGTA and subjected to sodium dodecylsulfate polyacrylamide gel electrophoresis and staining with Commassie blue. Lane 1 of the gel is the molecular weight marker; lane 2 is the eluate from the control column; and lane 3 is the eluate from the cromolyn column (arrow, S100P). The gel shown is one of three independent experiments.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure, according to specific example embodiments, generally relates to methods of inhibiting the interaction between a S100 molecule and the receptor for advanced glycation end-products (RAGE). In particular, the present disclosure relates to inhibiting the interaction between a S100 molecule and RAGE using cromolyn compounds and/or a C5 compound.

S100 molecules are part of a family of proteins, which include, inter alia, S100B, S100A12, and S100P. S100P has recently been found to be overexpressed in pancreatic, breast, and lung cancer. S100P is a 95-amino acid member of the S100 family of proteins. S100P is functionally important for pancreatic cancer cell growth and survival, in that it has been previously observed that levels of cellular S100P affect the rate of tumor growth in vivo and resistance of pancreatic cancer cells against 5-fluorouracil (5FU) treatment in vitro. In colon cancer cell lines, S100P levels are associated with resistance to chemotherapy. In lung cancer, S100P levels are associated with decreased patient survival. S100P is also associated with increased metastasis and decreased patient survival in breast cancer.

S100P is secreted by pancreatic cancer cells and acts extracellularly through interactions with a cell surface protein receptor for advanced glycation end-products (RAGE). RAGE is a multiligand receptor that interacts with a variety of molecules, including advanced glycation end-products, S100 molecules (S100B, S100A12, S100P), amyloid, and amphoterin. RAGE participates in a number of important pathologic processes, including Alzheimer disease, diabetes, inflammation, and cancer. Activation of RAGE by a S100 molecule stimulates several cellular signaling pathways, including the MAP kinase and NFκB pathways. NFκB signaling may be of particular importance because basal NFκB activity is elevated in the majority of pancreatic cancers and elevated NFκB activity is associated with increased resistance to therapies. NFκB activity is high in the majority of pancreatic cancers, in which it mediates anti-apoptotic signaling. Inhibition of NFκB has been shown to improve the effectiveness of cytotoxic agents in pancreatic cancer cells. Therefore, interventions that block the ability of S100 molecules to activate RAGE may provide a therapeutic benefit.

Cromolyn is widely used for the prophylactic treatment of allergic asthma. Cromolyn is commonly considered a mast cell stabilizer based on its ability to prevent secretion from some mast cells. However, the specific mechanisms of cromolyn's actions on mast cells are uncertain. An attractive model for the actions of cromolyn on mast cells is based upon its ability to interact with a component of a regulated $Ca^{2+}$ channel and prevent $Ca^{2+}$ entry and mast cell secretion. There are several observations, however, that do not fit this model. First, not all mast cells are inhibited by cromolyn. Cromolyn interferes with secretion specifically in rat peritoneal mast cells but not rat intestinal mucosal mast cells. Second, the inhibitory effects of cromolyn are not $Ca^{2+}$ dependent in either mast cells or in macrophages. Other suggested targets of cromolyn actions have included moesin, $Cl^-$ channels, protein kinase c, and nucleotide diphosphate kinase. But because cromolyn is impermeant to cells, interactions with intracellular molecules are unlikely to account for its biologic activity. Recently, cromolyn has been shown to bind with high affinity to $Ca^{2+}$ binding molecules belonging to the S100 family. It is currently unclear whether interactions with S100 molecules influence the actions of cromolyn on mast cells.

S100 molecules are small (9-12 kD) calcium-binding proteins that display 30-50% homology within the family. There are at least 19 members of the S100 family and most map closely together on chromosome 1q21, with the exception of S100P, which is located on 4p16. Cromolyn has previously been found to bind S100s A1, B, A12, and A13. Thus, cromolyn likely binds to structural features common to many of the S100 family members.

S100 proteins are involved in the regulation of a number of cellular processes. Some of these molecules also have roles in inflammatory responses. Recently, interest has been growing in the involvement of S100 proteins in cancer because of their differential expression in a variety of tumors. The expression of several S100 proteins has previously been observed in pancreatic tumors in profiling studies. It has been found that the S100 proteins A2, A4, A5, A6, A8, A9, A10, A11, A13, and A14 were expressed in both chronic pancreatitis and pancreatic cancer samples. In contrast, the S100P isoform was highly expressed only in pancreatic cancer.

Cromolyn and/or a C5 compound are useful as a inhibitor of the S100 activation of RAGE. The methods disclosed herein may provide for the inhibition of interactions between a S100 molecule with RAGE by the binding of cromolyn to a S100 molecule. The S100 molecule may be S100B, S100P, or another S100 molecule to which cromolyn may bind.

The methods provided herein may also provide for the inhibition of interactions by binding the C5 compound to a S100 molecule. The S100 molecule may be S100B, S100P, or another S100 molecule to which C5 compound may bind. Indeed, both cromolyn and C5 may bind to a S100 molecule including S100B, S100P, or another S100 molecule to which cromolyn and C5 may bind. Cromolyn and/or C5 bound to a S100 molecule may inhibit the S100 interactions with RAGE, as shown by a reduction in the level of co-immunoprecipitated S100 and RAGE complexes, and decreases S100-mediated increases in cancer cell growth, survival, and invasiveness in vitro. Cromolyn and/or C5 may also be used to inhibit basal activity of the NFκB pathway in pancreatic cancer cells with endogenous S100. C5 may also be useful in treating a variety of allergic diseases and inflammation.

Certain methods of the present disclosure comprise the step of administering a cromolyn compound of the Formula (I), or a salt, hydrate, or solvate thereof:

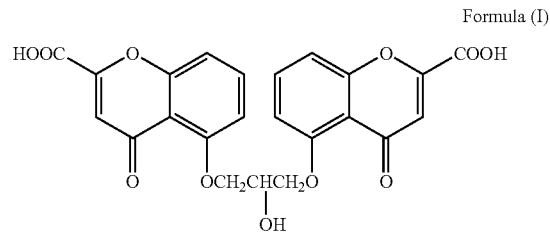

Formula (I)

The compound represented by Formula (I) that may be used in conjunction with the methods of the present disclosure may be disodium 1,3-bis[(2'-carboxylatochromon-5'-yl)oxy]-2-hydroxypropane.

The methods of the present disclosure further comprise administering to a patient in need thereof a C5 compound represented by the following Formula (II), or a salt, hydrate, or solvate thereof:

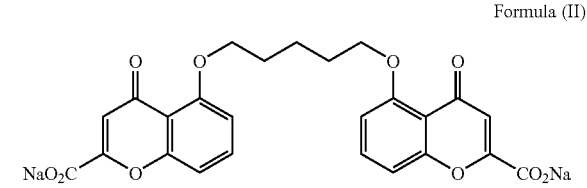

Formula (II)

The compound represented by Formula (II) that may be used in conjunction with the methods of the present disclosure may be disodium 1,5-bis(2-carboxychromon-5-yloxy) pentane.

The compounds represented by Formula (I), Formula (II), and/or a pharmaceutically acceptable salt or hydrate or solvate thereof, may be administered to a mammal, including a human, to inhibit the interaction between a S100 molecule and RAGE, among other things, to treat a cancer. Cromolyn and/or C5 may bind to an S100 molecule such as S100P or S100B.

The administration method may include, for example, oral or parenteral.

A compound represented by Formula (I), Formula (II), or a pharmaceutically acceptable salt or hydrate or solvate thereof, may be useful for the treatment or disorders of a wide variety of conditions where inhibition of the interaction between a S100 molecule and RAGE is useful. Disorders or conditions advantageously treated by the compounds of the subject invention include the prevention or treatment of cancer, such as pancreatic cancer, colorectal cancer, melanoma, and cancer of the breast, lung, prostate, ovary, colon, bladder, cervix and skin. Compounds of the invention may be used in the treatment and prevention of neoplasias including but not limited to brain cancer, bone cancer, a leukemia, a lymphoma, epithelial cell-derived neoplasia (epithelial carcinoma) such as basal cell carcinoma, adenocarcinoma, gastrointestinal cancer such as lip cancer, mouth cancer, esophogeal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body. The neoplasia can be selected from gastrointestinal cancer, liver cancer, bladder cancer, pancreas cancer, ovary cancer, prostate cancer, cervical cancer, lung cancer, breast cancer and skin cancer, such as squamous cell and basal cell cancers.

The compound represented by Formula (I), Formula (II), or a pharmaceutically acceptable salt or hydrate or solvate thereof, may be administered together and/or in conjunction with other cytotoxic drugs, including gemcitabine, a known cancer treatment. While it may be possible for the compounds can be administered as the raw chemical, it is also possible to present them as a pharmaceutical formulation. Accordingly, a pharmaceutical formulation is further provided comprising a compound or a pharmaceutically acceptable salt, ester, prodrug or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions of the present invention may be manufactured in a manner that is itself known, e.g., by means of conventional mixing, dissolving, granulating, dragee-making, levigating, emulsifying, encapsulating, entrapping or compression processes.

The pharmaceutical formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of the subject invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation. Formulations suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

The compound of Formula (I) and Formula (II) may be used to inhibit the interaction between a S100 molecule and the receptor for advanced glycation end-products (RAGE) in a dose dependent manner. It will be recognized by one of skill in the art that the optimal quantity and spacing of individual dosages of a compound represented by Formula (I) or Formula (II) will be determined by the nature and extent of the condition being treated, the form, route and site of administration, and the particular patient being treated, and that such optimums can be determined by conventional techniques. Similarly, the optimal course of treatment, for example, the number of doses of a compound represented by Formula (I) or Formula (II) given per day for a defined number of days, can be ascertained by those skilled in the art using conventional course of treatment determination tests.

Hence, the compounds presented herein can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for cancer involving administration of one of the compounds described herein, increased therapeutic benefit may result by also providing the patient with another therapeutic agent for cancer. In any case, regardless of the disease, disorder or condition being treated, the overall benefit experienced by the patient may simply be additive of the two therapeutic agents or the patient may experience a synergistic benefit.

To facilitate a better understanding of the present invention, the following examples of specific embodiments are given. In no way should the following examples be read to limit or define the entire scope of the invention.

EXAMPLES

Cell Culture and Treatment

Panc-1 and BxPC-3 pancreatic adenocarcinoma cells were obtained from the American Type Culture collection (Manassas, Va.). Mpanc-96 pancreatic adenocarcinoma cell lines were originally established by Dr. Timothy J Eberlein (St. Louis, Mo.) as described in Peiper M, et al., Human pancreatic cancer cells (MPanc-96) recognized by autologous tumor-infiltrating lymphocytes after in vitro as well as in vivo tumor expansion, Int. J. Cancer 1997 Jun. 11; 71(6):993-9. BxPC-3 cells were cultured in RPMI-1640 with 10% fetal bovine serum (FBS). Panc-1 and MPanc 96 cells were routinely cultured in DMEM with 10% FBS. All cells were maintained at 37° C. in a humidified atmosphere of 5% $CO_2$.

Cromolyn (sodium salt) was purchased from Sigma (St Louis, Mo.) as a sterile white powder in glass vials and stored at room temperature. For in vitro experiments, a stock solution of cromolyn (1 mM) was prepared in culture media. For in vivo experiments, cromolyn was dissolved at 50 mg per mL of phosphate-buffered saline (PBS; 0.025 M $Na_2HPO_4$, 0.025 M $NaH_2PO_4$ in 0.87% of NaCl). The reconstituted solution was clear and colorless. Platelet-derived growth factor (PDGF) was purchased from Sigma (St Louis, Mo.) and reconstituted in sterile-filtered 4 mM HCl containing 0.1% BSA to prepare a stock solution of 10 μg/mL, aliquotted, and stored in −20° C.

S100P Expression and Purification

S100P protein was expressed and purified as described in Arumugam, et al., S100P stimulates cell proliferation and survival via receptor for activated glycation end products (RAGE); J. Biol. Chem. 2004 Feb. 13; 279(7):5059-65. Briefly, full-length human S100P cDNA (NM_005980) was cloned into the pTrcHis2 vector (Invitrogen, Carlsbad, Calif.) and S100P expression was induced in vector-transformed bacteria by adding 1 mM of isopropyl-1-thio-β-D-galactopyranoside. His-tagged S100P was purified using a probond resin column, according to the manufacturer's instructions (Invitrogen, Carlsbad, Calif.). Briefly, the bacterial lysate containing S100P was loaded into the column and incubated for 60 minutes using gentle agitation to allow S100P to bind with the resin. Non-specific proteins were removed with wash buffer (50 mM $NaH_2PO_4$, 0.5 M NaCl, 20 mM imidazole, pH 8.0), and S100P was eluted using elution buffer (50 mM $NaH_2PO_4$, 0.5 M NaCl, 250 mM imidazole, pH 8.0) and stored at −80° C. with 5% sterile glycerol. The purity of the S100P protein was approximately 95%, as indicated by sodium docecyl-sulfate polyacrylamide gel electrophoresis (SDS-PAGE) and immunoblotting. The purified S100P was found to be free from endotoxin (LPS) contamination, as indicated by a Limulus amebocyte gel formation assay using gram-negative bacteria LPS as a standard (Cambrex, Walkersville, Md.). Proteins isolated from non-induced bacteria were used as an additional negative control. Before use in cell culture, S100P was diluted in culture medium for use at the indicated concentrations.

S100P Binding to Cromolyn Using Affinity Chromatography

Cromolyn was coupled to AF-TOYOPEARL resin as described in Shishibori, et al., Three distinct anti-allergic drugs, amlexanox, cromolyn and tranilast, bind to S100A 12 and S100A13 of the S100 protein family; Biochem. J. 1999 Mar. 15; 338 (Pt 3):583-9. Briefly, 0.1 grams of cromolyn was dissolved in 1 mL of N,N-dimethylformamide and added to 7 mL (5 grams wet mass) AF-TOYOPEARL. Next, 0.5 grams of N-ethyl-N-(3-dimethylaminopropyl) carbodiimide hydrochloride, suspended in 10 mL of N,N-dimethylformamide, was added to the cromolyn+AF-TOYOPEARL slurry. The pH was adjusted to 5.0, and the slurry was incubated with gentle shaking for 48 hours at 25° C. As a negative control, a column was prepared by blocking the amino group of AF-TOYOPEARL with sodium acetate and acetic anhydride. Purified His-tagged S100P was applied to the cromolyn-coupled and control columns, which had been equilibrated previously with equilibration buffer (20 mM Tris-HCl, 0.5 mM CaCl, pH 7.5). The columns were then washed once with 15 mL of wash buffer (20 mM Tris-HCl, 0.2 mM CaCl, pH 7.5) to remove unbound proteins, and bound proteins were eluted with 15 mL of elution buffer (20 mM Tris-HCl, 2.0 mM EGTA, pH 7.5). The eluted protein fraction was concentrated using a protein concentration column YM-3 (Millipore, Bedford, Mass.), separated by 15% SDS-PAGE analysis, and stained with 0.1% Coomassie blue. The cromolyn affinity column (FIG. 1A, lane 3), but not the control column (FIG. 1A, lane 2), retained S100P, indicating a specific interaction.

Co-Immunoprecipitation of S100P and RAGE

For co-immunoprecipitation experiments, BxPC-3 cell lysates were incubated in the absence or presence of cromolyn (100 μM) at 4° C. overnight. S100P was immunoprecipitated using a mouse monoclonal anti-S100P antibody (Transduction Laboratories, San Diego, Calif.) for 6 hours at 4° C. and IgG-immobilized beads (Pierce Biotechnology, Inc. Rockford, Ill.). Antibody-associated proteins were electrophoresed on 10% polyacrylamide gels and electrophoretically transferred to nitrocellulose membranes. Membranes were blocked in PBS/5% milk overnight at 4° C. RAGE was detected using a goat polyclonal anti-RAGE antibody (1:200, Santa Cruz, Santa Cruz, Calif.), and S100P was detected using a goat polyclonal anti-S100P antibody (1:50, R & D systems, Minneapolis, Minn.) by immunoblotting as described in Arumugam, et al., S100P stimulates cell proliferation and survival via receptor for activated glycation end products (RAGE); J. Biol. Chem. 2004 Feb. 13; 279(7):5059-65. Briefly, membranes were incubated in primary antibody for 1 hour at room temperature followed by incubation with horseradish peroxidase-labeled secondary antibody for 30 minutes at room temperature. After a thorough wash in TBS-T buffer (1M Tris-HCL pH 8.3, 3M NaCl, 0.1% Tween-20), antibody-protein complexes were detected by using a chemiluminescent substrate (GE Healthcare Bio-Sciences Corp., Piscataway, N.J.). The intensity of the band was estimated (as density units) using densitometry (GS-250 Molecular Imaging System, Bio-Rad Laboratories, Richmond, Calif.). The experiment was repeated three times.

Figure 1B:
FIG. 1B shows an immunoblotting in the upper panel where BxPC-3 pancreatic cancer cell lysates were immunoprecipitated (IP) with mouse monoclonal anti-S100P antibody (IP α-S100P) in the presence and absence of cromolyn (100 μM). Receptor for advanced glycation end products (RAGE) was identified in the immunoprecipitates by immunoblotting with a goat polyclonal anti-RAGE antibody and anti-S100P as an internal control. In the lower panel, one representative blot and densitometric analysis (means and 95% confidence intervals [CIs]) of three independent experiments is shown. *P<0.001, versus IP α-S100P without cromolyn.

Our previous studies indicated that S100P co-immunoprecipitates with RAGE. To determine the influence of cromolyn on this interaction, lysates from BxPC-3 cells were immunoprecipitated with a mouse monoclonal anti-S100P antibody in the presence or absence of cromolyn. The immunoprecipitated proteins were subjected to immunoblotting with an anti-RAGE antibody. See FIG. 1B. RAGE was identified in the precipitate, confirming the interaction between S100P and RAGE. Inclusion of cromolyn (100 μM) resulted in statistically significant reduction in the co-immunoprecipitation of S100P and RAGE (control, mean=34040 versus cromolyn, mean=8410 density units, difference=25640 density units, 95% CI=18641 to 32638 density units, P<0.001, FIG. 1B), suggesting that cromolyn interfered with the interaction. In contrast, cromolyn had no effect on the total amount of S100P immunoprecipitated (FIG. 1B), indicating that cromolyn did not interfere with the interaction between S100P and the monoclonal antibody and that equal amounts of protein were loaded on the gel.

Figure 1C:
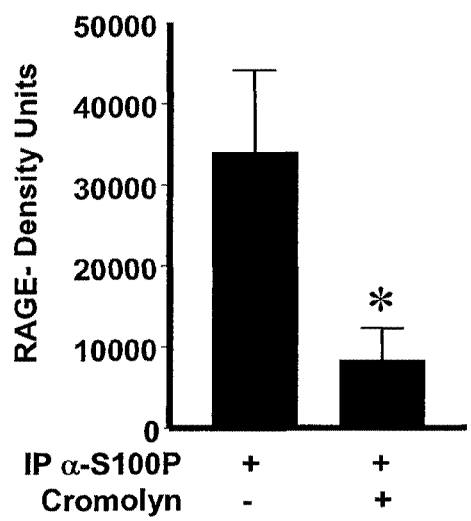
FIG. 1C shows the effect of cromolyn on cell proliferation. Panc-1 pancreatic adenocarcinoma cells ($1.0 \times 10^3$ cells/well) were cultured in the presence or absence of S100P (100 nM) and with or without cromolyn (100 μM), and cell proliferation was analyzed at 24, 48, and 72 hours. Means and 95% confidence intervals of three independent experiments performed in triplicate are shown. *, P=0.001, S100P alone versus S100P+cromolyn.
Figure 1C:
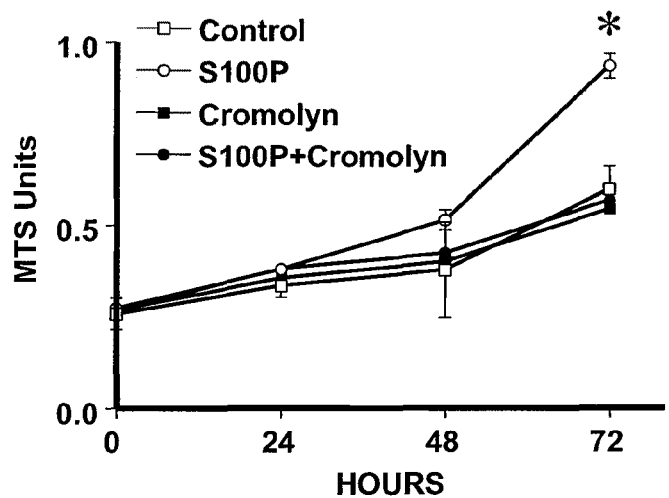
Figure 1D:
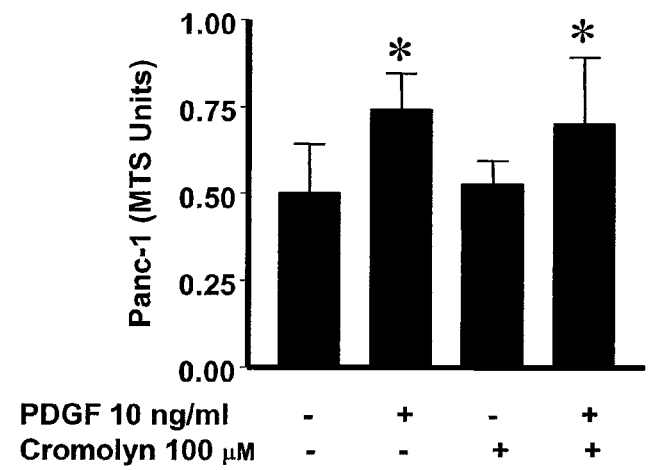
FIG. 1D shows the effect of cromolyn on cell proliferation. Panc-1 cells were plated at $1.0 \times 10^3$ cells/well and treated with platelet-derived growth factor (10 ng/mL) with or without cromolyn (100 μM), and cell proliferation was analyzed after 48 hours. Means and 95% confidence intervals of three independent experiments performed in triplicate are shown. *, P=0.004 PDGF and P=0.022 cromolyn+PDGF versus control.
Figure 1E:
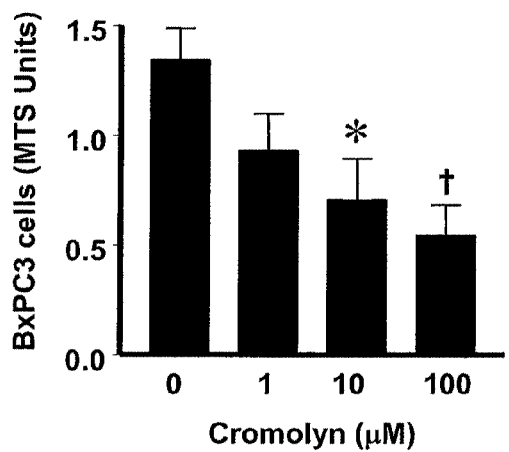
FIG. 1E shows the effect of cromolyn on cell proliferation. BxPC-3 cells were plated at $1.0 \times 10^3$ cells/well and treated with 0 μM, 1 μM, 10 μM, and 100 μM of cromolyn, and cell proliferation was analyzed after 48 hours. Means and 95% confidence intervals of three independent experiments performed in triplicate are shown. *, P=0.002; †, P<0.001 versus control.

To determine whether inhibiting the interaction between S100P and RAGE would influence cancer cell growth, the effects of cromolyn on pancreatic cancer cells in vitro were tested. The effects of cromolyn both on cells that lack endogenous S100P (Panc-1) and those that express high levels of endogenous S100P (BxPC-3) were examined. Cromolyn treatment alone had no effect on cell proliferation of Panc-1 cells, indicating a lack of non-specific toxic effects. See FIG. 1C. However, cromolyn completely blocked the effects of exogenous S100P treatment (S100P, mean=0.93 versus S100P+cromolyn [100 µM], mean=0.56 MTS units, difference=0.37 MTS units, 95% CI=0.25 to 0.49 MTS units; P=0.001, FIG. 1C). To further investigate the specificity of cromolyn's effects, platelet-derived growth factor (PDGF) stimulation of Panc-1 cell proliferation in the presence of cromolyn was examined. PDGF statistically significantly increased Panc-1 cell growth (control, mean=0.5 versus PDGF, mean=0.7 MTS units, difference=0.2 MTS units, 95% CI=0.1 to 0.3 MTS units; P=0.004, FIG. 1D). Cromolyn had no inhibitory effect on basal growth of Panc-1 cells nor did it inhibit growth stimulation caused by PDGF (FIG. 1D). Likewise, cromolyn did not influence serum stimulated Panc-1 cell proliferation. These data suggest that cromolyn does not have non-specific effects on Panc-1 cell growth. In contrast, in BxPC-3 cells, cromolyn inhibited basal rates of cell proliferation in a concentration-dependent manner (0 µM, mean=1.2 versus 10 µM, mean=0.7 MTS units, difference=0.5 MTS units, 95% CI=0.3 to 0.7 MTS units; P=0.002, 100 µM, mean=0.6 MTS units, difference=0.6 MTS units, 95% CI=0.4 to 0.8 MTS units; P<0.001, FIG. 1E). These data suggest that autocrine activation of RAGE by S100P contributes to basal cell proliferation in this cancer cell line. Similar results were found with MPanc-96 cells, which also express endogenous S100P. Thus, cromolyn was able to block the effects of both exogenous and endogenous S100P on pancreatic cancer cell proliferation.

Figure 1F:
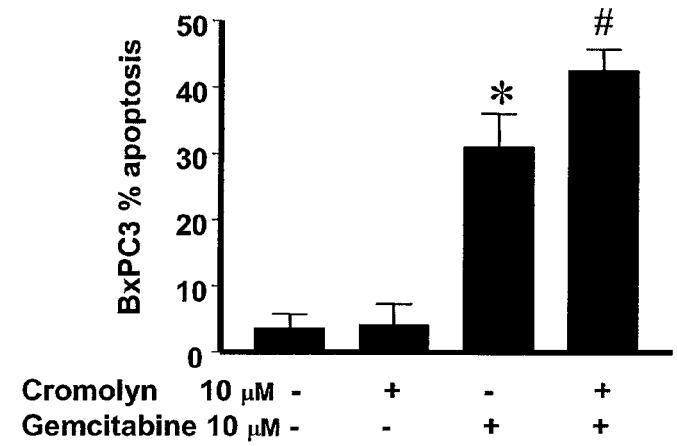
FIG. 1F shows the effect of cromolyn on cell proliferation. BxPC-3 cells were treated with cromolyn (10 μM) with (+) or without (−) gemcitabine (10 μM), and apoptosis was analyzed after 48 hours by flow cytometry. *, P<0.001 versus control, #, P=0.001 versus gemcitabine. Means and 95% confidence intervals of three independent experiments performed in triplicate are shown. Two-tailed two-sample (unpaired) Student's t-tests were used to determine P values.

It has been previously found that S100P provides a survival advantage for pancreatic cancer cells. Therefore, it was examined whether cromolyn would influence the responsiveness of BxPC-3 cells to gemcitabine-induced apoptosis. As expected, treatment with gemcitabine resulted in statistically significant cell death (control, mean=3.7% versus gemcitabine, mean=31.0%, difference=27.3%, 95% CI=23.8% to 30.8%; P<0.001, FIG. 1F). In contrast, cromolyn was not toxic to the cells and had no statistically significant effect on BxPC-3 cell apoptosis (FIG. 1F). However, in combination with gemcitabine, cromolyn statistically significantly increased cell death (gemcitabine, mean=30.8% versus combination, mean=42.6% of cells were apoptotic, difference=11.6%, 95% CI=7.8 to 15.4%; P=0.001, FIG. 1F).

Figure 2A:
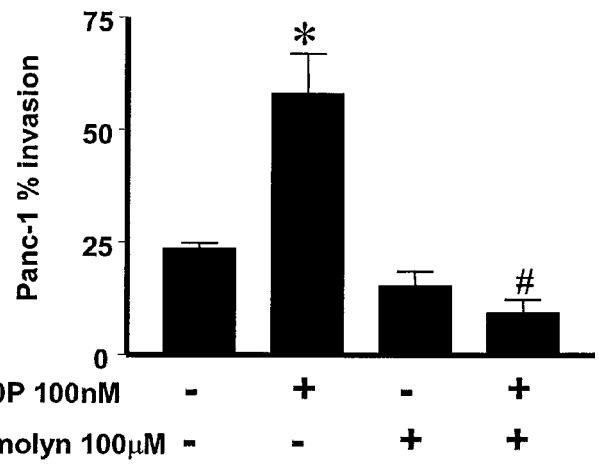
FIGS. 2A-2D show the effect of cromolyn on pancreatic cancer cell invasion. Panc-1 and BxPC-3 cells were plated in Bio-coat matrigel and control chambers and cultured in serum-free culture media. After 24 hours non-invaded cells in the upper chamber were removed, and cells that invaded onto the lower surface of the membrane were counted from five adjacent fields.
Figure 2B:
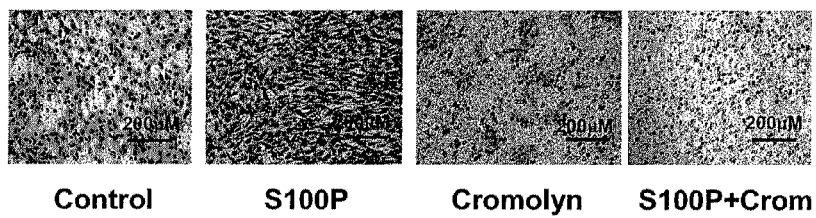
Figure 2C:
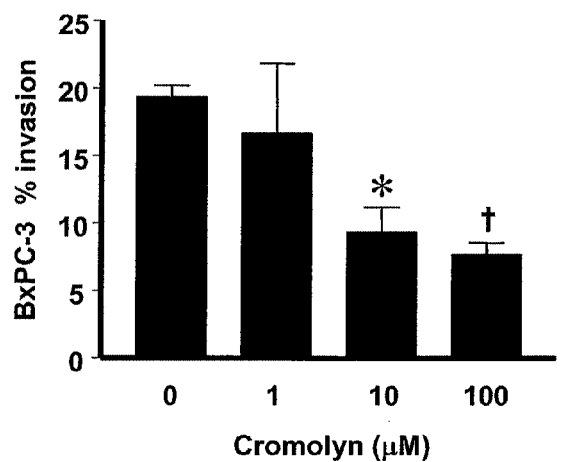
Figure 2D:
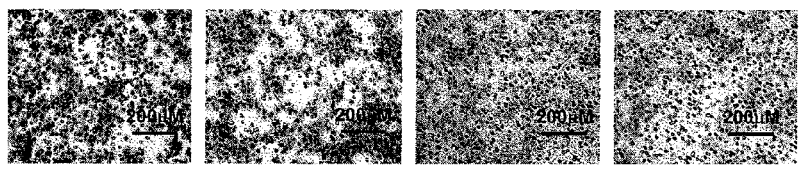

It has been previously found that S100P increases migration and invasion of pancreatic cancer cells. Therefore, the effects of cromolyn on pancreatic cancer cell invasion with matrigel assays were examined. In Panc-1 cells, which do not express S100P, cromolyn did not reduce basal cell invasion. However, cromolyn did block the effects of exogenous S100P on Panc-1 cell invasion (S100P, mean=58.0% versus S100P+ cromolyn, mean=9.4% of cells invaded, difference=48.6%, 95% CI=38.8 to 58.8%; P<0.001, FIGS. 2A and 2B). By contrast, in BxPC-3 cells, which express S100P endogenously, cromolyn inhibited basal cell invasiveness in a concentration-dependent manner (0 µM, mean=19.3% versus 10 µM, mean=9.3% of cells invaded, difference=10.0%, 95% CI=4.5 to 15.5%; P=0.008, 100 µM, mean=7.7%, difference=11.7%, 95% CI=8.2 to 15.2%; P<0.001, FIGS. 2C and 2D). Likewise, cromolyn also inhibited basal cell invasiveness of MPan-96 cells. These data further indicate that cromolyn can inhibit both endogenous and exogenous S100P actions.

Cell Growth Studies

Growth of Panc-1 and BxPC3 pancreatic adenocarcinoma cells was analyzed using MTS reagent (Promega, Madison, Wis.) according to the manufacturer's directions. Purified S100P (100 nM final concentration) with or without cromolyn (100 µM final concentration) was added to Panc-1 cells. Only cromolyn (0-100 µM) was added to BxPC-3 cells, which express endogenous S100P. For both cell models, $1.0 \times 10^3$ cells/well were plated in 96-well culture dishes. Cells were treated with S100P, PDGF, or cromolyn, or a combination, followed immediately by treatment with either S100P or PDGF. MTS (20 µL per well) was added to cells at various times, and the mixture was incubated for 1 hour at 37° C. Samples were then read at 490 nm (as O.D. units) on a uQuant-Microplate Spectrophotometer (Bio-Tek Services Inc., Richmond, Va.). The assay was performed three times in triplicate.

Development of Stable Cell Lines

To study pancreatic cancer cell NFκB activity, a lentivirus NFκB luciferase reporter gene construct was developed. The NFκB luciferase reporter gene was excised and isolated from the pNF-κB-Luc Vector (Clonetec, Mountain View, Calif.) and cloned into the lentiviral vector FG9 (Gift from Dr. Xiao-Feng Qin, Dept. of Immunology, M.D. Anderson Cancer Center replacing the CMV/LTR and UBiC promoters, to form Lenti-NFκB-Luc. Lentiviral NFκB vector were co-transfected with packaging constructs pRSVREV, pMDLg/pRRE, and the VSV-G expression plasmid pHCMVG, and lentivirus was produced in 293T cells by the calcium transfection method, as previously described in Qin, et al., Inhibiting HIV-1 infection in human T cells by lentiviral-mediated delivery of small interfering RNA against CCR5; Proc. Natl. Acad. Sci. U.S.A. 2003 Jan. 7; 100(1):183-8. Lenti-NFκB-Luc was titrated, and Panc-1 cells, which lack endogenous S100P, and BxPC-3 cells, which possess high levels of endogenous S100P, were each infected with Lenti-NFκB-Luc virus (25 µL viral supernatant/mL of medium) mixed with polybrene (4 µg/mL medium). Functional validation of NFκB reporter activity was conducted in vitro using TNF-α (20 ng/mL, Sigma, St. Louis, Mo.) as a positive control.

To study pancreatic cancer growth in vivo, a lentiviral luciferase construct (without NFkB) was developed. The luciferase coding sequence was isolated from the pGL-3 Vector (Promega, Madison, Wis.) and cloned into the lentiviral vector FG9 behind the CMV/LTR and UBiC promoter to form the luciferase expressing lentivirus (Lenti-Luc). Viral particles were produced as described above using packaging vectors. Cells were infected with Lenti-luc virus (25 µL viral supernatant/mL of medium) mixed with polybrene (4 µg/mL medium). Luciferase expression was confirmed in $0\text{-}10 \times 10^5$ cells/well in a 24-well plate by measuring the light emission after adding luciferin (150 µg/mL) using the IVIS system (Xenogen Corp., Alameda, Calif.) and emitted light was directly proportional to the number of cells.

Flow Cytometry to Measure Apoptosis

Standard propidium iodide (PI) staining by the hypotonic lysis method was used for apoptosis studies. Apoptosis was induced in $1.0 \times 10^6$ BxPC-3 cells by treatment with gemcitabine (10 μM), with or without cromolyn. After 48 hours the cells were detached from culture dishes by incubation in 0.05% trypsin-EDTA, washed once with cold PBS, and then incubated for 30 minutes in 500 μL of hypotonic solution (0.1% sodium citrate, 0.1% Triton X-100, 100 μg/mL RNAse, and 50 μg/mL PI), and analyzed by flow cytometry (EPICS XL, Beckman Coulter Inc, Fullerton, Calif.). Cells undergoing apoptosis that had lost part of their DNA were identified as the population of cells with sub-G1 DNA content. These assays were performed three times.

Invasion Assays

Panc-1 and BxPC-3 cells were seeded in BIOCOAT matrigel invasion chambers and in control chambers without matrigel (Becton-Dickinson, Bedford, Mass.) according to the manufacturer's protocol. Panc-1 cells were seeded with S100P (100 nM) with or without cromolyn (100 μM), and BxPC-3 cells were seeded with or without cromolyn (1-100 μM). Briefly, $2.0 \times 10^5$ cells in 300 μL top solution (serum-free media) were added to each chamber and allowed to invade matrigel for 24 hours at 37° C. in a 5% $CO_2$ atmosphere. The non-invading cells on the upper surface of membrane were removed from the chambers with a cotton swab, and the invading cells on the lower surface of the membrane were fixed and stained using a Diff-Quick stain kit (Becton Dickinson, Bedford, Mass.). After two washes with water, the chambers were allowed to air dry. The numbers of invading cells in five adjacent microscope fields per membrane were counted at 20× magnification to obtain the average number of cells per field. Data are expressed as the percent invasion through the matrigel matrix and membrane relative to the migration through the control membrane. The assays were performed three times.

Luciferase Assay for NFκB Activity

BxPC-3 and Panc-1 cells stably expressing a Lenti-NFkB-luc reporter construct were treated with S100P, cromolyn, or the combination for 5 hours. D-luciferin (150 μg/mL) was added to the cells, and luciferase activity was measured using an IVIS bioluminescence system (Xenogen Co. Alameda, Calif.). Each experiment was conducted three times in triplicate.

To measure NFκB promoter activity in vivo, BxPC-3 cells (50,000/50 μL) stably expressing a Lenti-NFkB-luc reporter were transplanted orthotopically into the pancreas of 4-week-old male CB 17 scid mice (n=4 mice per experiment). After 1 week mice were injected with D-luciferin (150 mg per kg body weight, i.p.), and basal NFκB activity was determined using the IVIS system. Subsequently, mice were injected with cromolyn (5 mg per kg body weight, i.p.), and NFκB luciferase activity was re-analyzed after 24 and 48 hours. These experiments were performed three times.

Figure 3A:
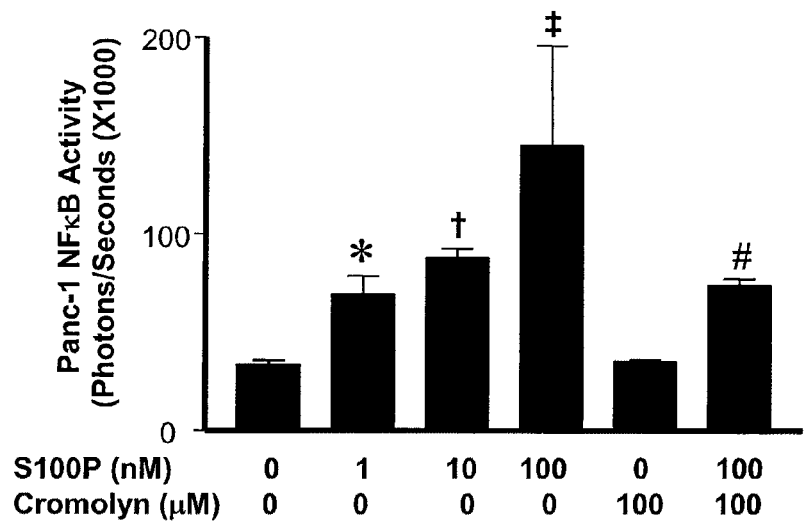
FIGS. 3A, 3B, and 3C show the effect of cromolyn on S100P stimulated NFκB promoter activity in pancreatic cancer cells in vitro and in vivo. Panc-1 and BxPC-3 pancreatic cancer cell lines stably expressing an NFκB luciferase reporter were examined for the effects of S100P and cromolyn.
Figure 3B:
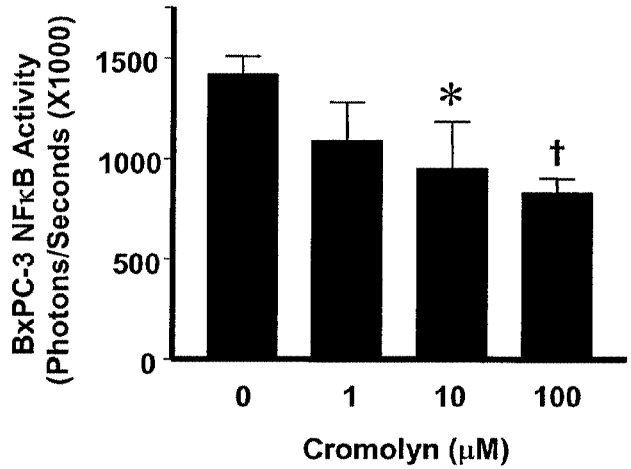

To determine whether cromolyn inhibited S100P stimulation of NFκB activity, the effects of cromolyn on S100P activation of an NFκB luciferase reporter gene construct in both Panc-1 and BxPC-3 cells in vitro were examined. In Panc-1 cells, which lack endogenous S100P, cromolyn had no effect on basal NFκB activity (FIG. 3A). However, S100P increased NFκB promoter activity in Panc-1 cells in a concentration-dependent manner (0 nM, mean=3358 versus 1 nM, mean=6902 photons/sec, difference=3544 photons/sec, 95% CI=852 to 6235 photons/sec; P=0.022; 10 nM, mean=8758 photons/sec, difference=5400 photons/sec, 95% CI=3968 to 6832 photons/sec; P<0.001; 100 nM, mean=14460 photons/sec, difference=11100 photons/sec, 95% CI=7771 to 14430 photons/sec; P<0.001) and cromolyn (100 μM) inhibited this effect (100 nM of S100P alone, mean=14460 versus combination, mean=7360 photons/sec, difference=7100 photons/sec, 95% CI=3689 to 10510 photons/sec; P=0.005). In BxPC-3 cells, which express endogenous S100P, cromolyn inhibited basal NFκB activity in a concentration-dependent manner (0 μM, mean=$1.4 \times 10^6$ versus 10 μM, mean=$9.4 \times 10^5$ photons/sec, difference=$4.7 \times 10^5$ photons/sec, 95% CI=$2.6 \times 10^5$ to $6.7 \times 10^5$ photons/sec; P=0.003; 100 μM, mean=$8.2 \times 10^5$ photons/sec, difference=$5.9 \times 10^5$ photons/sec, 95% CI=$5.1 \times 10^5$ to $6.6 \times 10^5$ photons/sec; P<0.001; FIG. 3B).

Figure 3C:
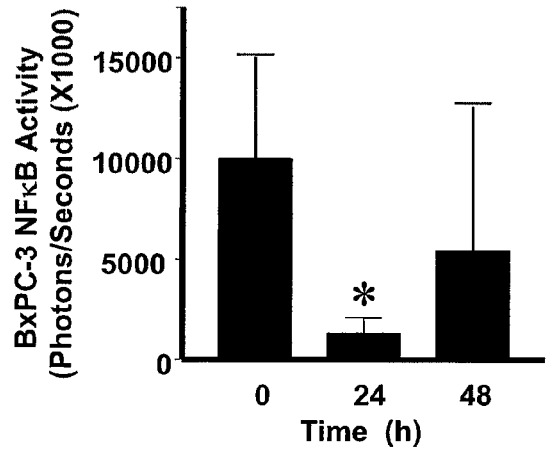

To determine whether cromolyn treatment could also reduce NFκB activity in vivo, NFκB activity of BxPC-3 cells stably expressing an NFκB luciferase reporter construct that had been transplanted orthotopically into the pancreas of nude mice (n=4) was examined. After 1 week, NFκB luciferase activity was determined before (0 time point) and at 24 and 48 hours after a single dose of cromolyn (5 mg per kg body weight by intraperitoneal [i.p.] injection). Cromolyn administration reduced basal NFκB activity by at least 80% 24 hours after injection (0 h, mean=$9.9 \times 10^6$ versus 24 h, mean=$1.3 \times 10^6$ photons/sec, difference=$8.6 \times 10^6$ photons/sec, 95% CI=$3.1 \times 10^6$ to $1.4 \times 10^7$ photons/sec; P=0.005, FIG. 3C). At 48 hours after cromolyn injection, NFκB activity returned to control levels. These data indicate that cromolyn inhibits, both in vitro and in vivo, basal NFκB levels of pancreatic cancer cells that express endogenous S100P.

Tumor Growth and Invasion Study in Scid Mice

The anti-tumorigenic capability of the drug cromolyn was assessed in 4-week-old male CB 17 scid mice (n=20) carrying orthopic tumors of BxPC-3, MPanc96, and Panc-1 cells stably expressing a Lenti-luc reporter. All mouse experiments were reviewed and approved by the Institutional Animal Care and Use Committee of UT MD Anderson Cancer Center. All mice were maintained in a sterile environment. Cages, bedding, food, and water were all autoclaved. All mice were maintained on a daily 12-hour light/12-hour dark cycle, according to the institutional animal welfare guidelines.

Figure 4D:
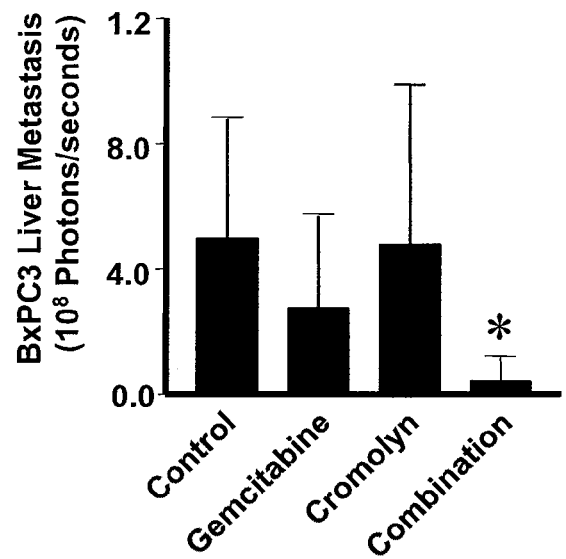
Figure 5A:
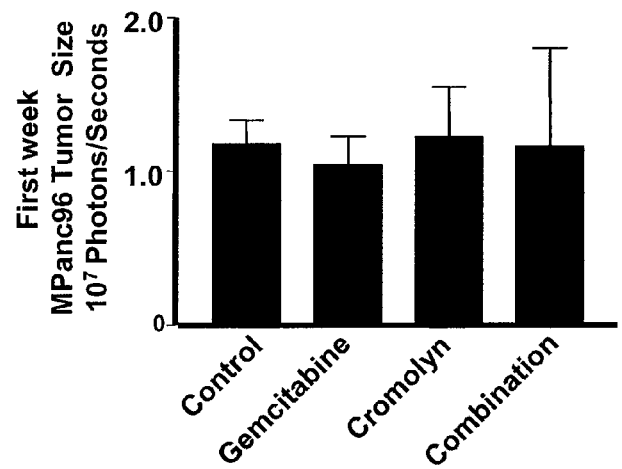
FIGS. 5A-5F show the effect of cromolyn on MPanc-96 tumor growth and metastasis in vivo. MPanc-96 cells stably expressing the firefly luciferase gene were injected orthotopically into 4-week-old male CB 17 scid mice.
Figure 5B:
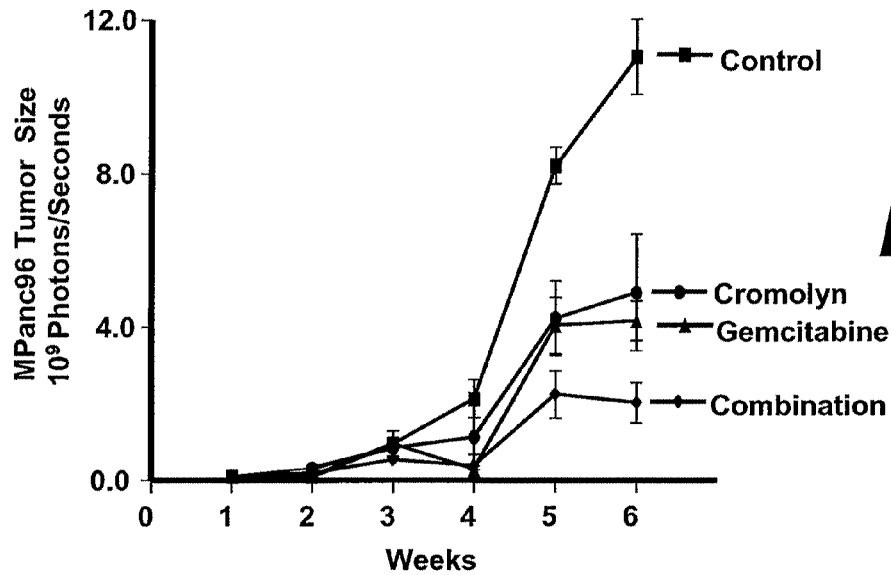
Figure 6A:
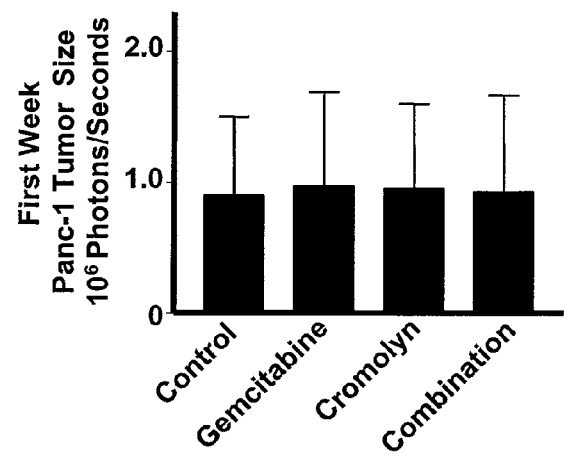
FIGS. 6A-6F show the effect of cromolyn on Panc-1 tumor growth and metastasis in vivo. Panc-1 cells stably expressing the firefly luciferase gene were injected orthotopically into 4-week-old male CB 17 scid mice.
Figure 6B:
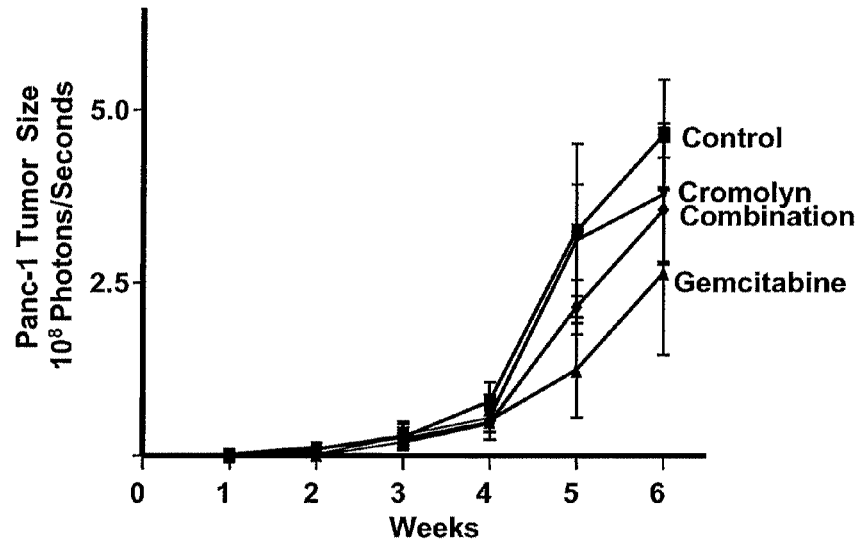

BxPC-3, MPanc96, and Panc-1 cells carrying the Lenti-luc reporter gene were grown to 80% confluence, harvested by incubation with trypsin-EDTA, washed twice in PBS, and resuspended to a final concentration of $4.0 \times 10^6$ cells/mL. Each mouse (n=20 mice per cell line) was injected (into the pancreas) with cell suspensions (50 μL). Bioluminescent imaging to determine tumor volume was performed 1 week after injection because the tumors became established within this amount of time. This initial tumor volume was used to divide the mice into four groups of five mice each, such that the mean tumor size was equal between groups (FIGS. 4A, 5A, and 6A). To allow enough time to observe differences among treatment groups, the mice were followed for the next 5 weeks. One group of mice was then treated biweekly with a sub-maximal concentration of gemcitabine (125 mg per kg body weight by i.p. injection). A second group was treated with a daily injection of cromolyn (5 mg per kg body weight by i.p. injection). A third group was treated with both biweekly gemcitabine and daily cromolyn. The control group was treated daily with vehicle. Treatments were continued for 5 weeks, and the effects on the tumor burden and metastasis were analyzed by weekly bioluminescence imaging (FIGS. 4B, 5B, and 6B). At the end of the experiment the mice were anesthetized with 1.5% isofluorane/air mixture and killed by cervical dislocation.

Bioluminescence imaging was conducted using a cryogenically cooled IVIS 100 imaging system coupled to a data acquisition computer running Living Image software (Xenogen Corp., Alameda, Calif.). Before imaging, mice were placed in an acrylic chamber, anesthetized with 1.5% isofluorane/air mixture, and injected i.p. with 15 mg/mL of luciferin potassium salt in PBS at a dose of 150 mg per kg body weight. A digital grey scale image of each mouse was acquired, followed by acquisition and overlay of a pseudocolor image representing the spatial distribution of detected photons emerging from active luciferase within the mouse. Tumor volume was quantified as the sum of all detected photons within the region of the tumor per second. At the end of experiment, the mice were killed, and tumors were surgically removed and weighed. After the primary tumors were removed, cancer cell dissemination and metastasis was visualized using IVIS imaging, and metastatic colonies were counted. Subsequently, tissues were fixed with formaldehyde, and histology was used to verify the accuracy of the bioluminescence data.

Figure 5C:
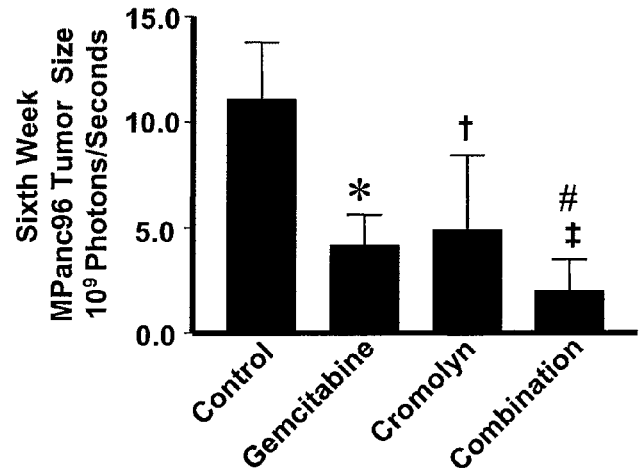
Figure 6C:
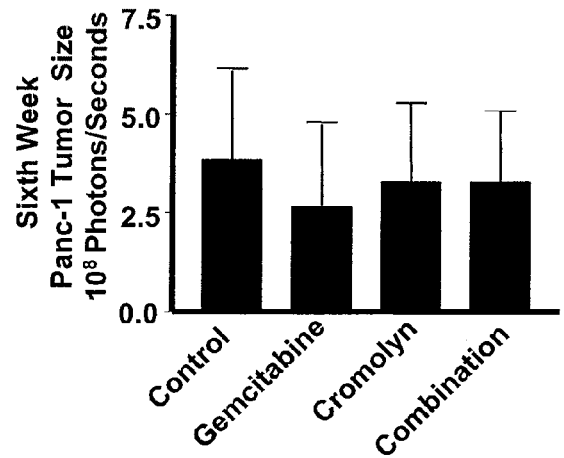

Gemcitabine strongly reduced the tumor burden relative to controls, in both the BxPC-3 (control, mean=$1.6 \times 10^9$ versus gemcitabine, mean=$9.2 \times 10^8$ photons/sec, difference=$6.8 \times 10^8$ photons/sec, 95% CI=$1.8 \times 10^8$ to $1.1 \times 10^9$ photons/sec; P=0.013; FIG. 4C) and the MPanc-96 (control, mean=$1.1 \times 10^{10}$ versus gemcitabine, mean=$4.1 \times 10^9$ photons/sec, difference=$6.9 \times 10^9$ photons/sec, 95% CI=$4.3 \times 10^9$ to $9.4 \times 10^9$ photons/sec P<0.001, FIG. 5C) models. Cromolyn also statistically significantly reduced tumor burden in the BxPC-3 (control, mean=$1.6 \times 10^9$ versus cromolyn, mean=$4.4 \times 10^8$ photons/sec, difference=$1.2 \times 10^9$ photons/sec, 95% CI=$6.2 \times 10^8$ to $1.6 \times 10^9$ photons/sec; P<0.001, FIG. 4C) and MPanc-96 (control, mean=$1.1 \times 10^{10}$ versus cromolyn, mean=$4.8 \times 10^9$ photons/sec, difference=$6.2 \times 10^9$ photons/sec, 95% CI=$1.9 \times 10^9$ to $1.0 \times 10^{10}$ photons/sec P=0.009, FIG. 5C) models, and this effect was similar in extent to that of gemcitabine. In combination, gemcitabine and cromolyn reduced tumor burden to a greater extent than gemcitabine alone in both the BxPC-3 (gemcitabine, mean=$9.2 \times 10^8$ versus combination, mean=$1.8 \times 10^8$ photons/sec, difference=$7.4 \times 10^8$ photons/sec, 95% CI=$4.5 \times 10^8$ to $1.0 \times 10^9$ photons/sec; P<0.001, FIG. 4C) and the MPanc-96 (gemcitabine, mean=$4.1 \times 10^9$ versus combination, mean=$2.0 \times 10^9$ photons/sec, difference=$2.1 \times 10^9$ photons/sec, 95% CI=$4.4 \times 10^8$ to $3.8 \times 10^9$ photons/sec; P<0.001, FIG. 5C) models. In contrast to these effects on pancreatic cancer cells that express endogenous S100P, cromolyn treatment did not reduce tumor development or increase the effectiveness of gemcitabine in a model involving Panc-1 cells, which do not express S100P (FIG. 6A-6C).

Figure 4E:
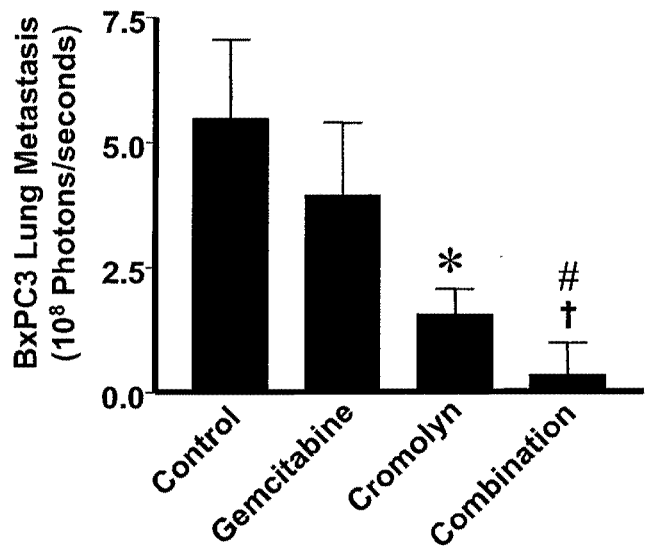
Figure 5D:
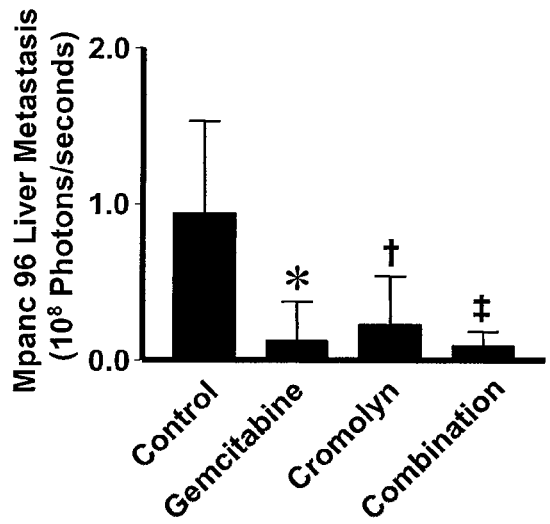
Figure 5E:
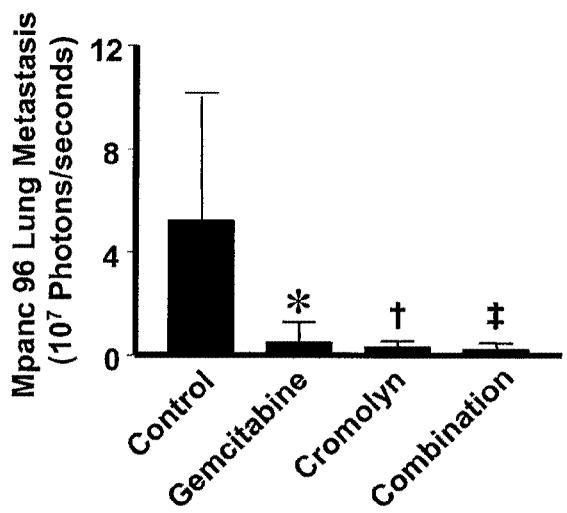

The effects of these treatments on tumor metastasis were also analyzed. In the BxPC-3 in vivo model, gemcitabine treatment alone did not reduce metastasis in either lung or liver compared with that in control mice. Cromolyn treatment statistically significantly reduced lung (control, mean=$5.5 \times 10^8$ versus cromolyn, mean=$1.6 \times 10^8$ photons/sec, difference=$3.9 \times 10^8$ photons/sec, 95% CI=$2.3 \times 10^8$ to $5.4 \times 10^8$ photons/sec; P=0.001, FIG. 5E) but not liver metastasis in this model. However, the combination of cromolyn and gemcitabine reduced metastasis in both lung and liver. For example, in the liver the combination reduced metastasis by more than 90% (control, mean=$5.8 \times 10^8$ versus combination, mean=$4.2 \times 10^7$ photons/sec, difference=$5.4 \times 10^8$ photons/sec, 95% CI=$3.7 \times 10^7$ to $1.0 \times 10^9$ photons/sec; P=0.04, FIG. 4D) compared with control. In the lung combination reduced metastasis to a greater extent than gemcitabine alone (gemcitabine, mean=$3.9 \times 10^8$ versus combination, mean=$3.6 \times 10^7$ photons/sec, difference=$3.5 \times 10^8$ photons/sec, 95% CI=$2.1 \times 10^8$ to $5.0 \times 10^8$ photons/sec; P=0.001, FIG. 4E).

Figure 6D:
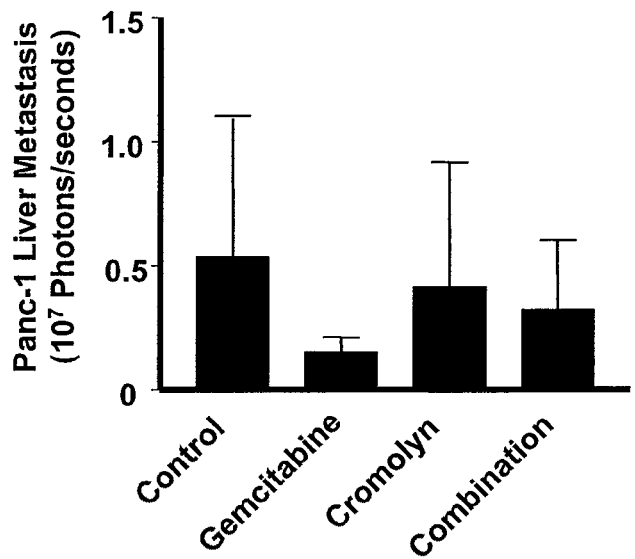
Figure 6E:
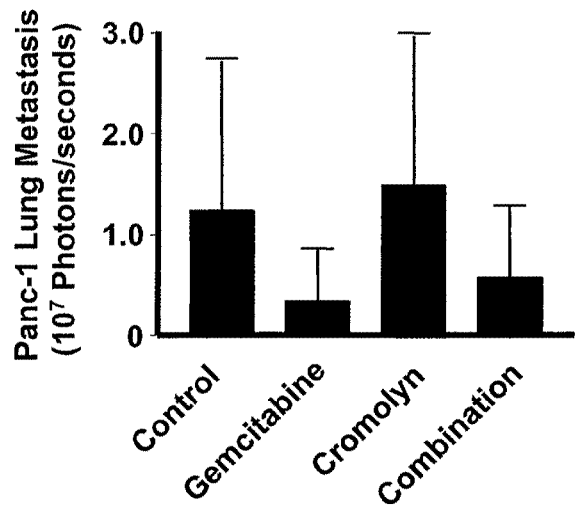

In the MPanc-96 in vivo model, gemcitabine treatment reduced metastasis both liver (control, mean=$9.4 \times 10^8$ versus gemcitabine, mean=$1.2 \times 10^8$ photons/sec, difference=$8.1 \times 10^8$ photons/sec, 95% CI=$2.2 \times 10^8$ to $1.4 \times 10^9$ photons/sec; P=0.014, FIG. 5D) and lung (control, mean=$5.9 \times 10^7$ versus gemcitabine, mean=$5.0 \times 10^6$ photons/sec, difference=$5.4 \times 10^7$ photons/sec, 95% CI=$6.4 \times 10^6$ to $1.0 \times 10^8$ photons/sec; P=0.03, FIG. 5E) metastasis. Cromolyn also reduced liver (control=$9.4 \times 10^8$ versus cromolyn=$2.2 \times 10^8$ photons/sec, difference=$7.2 \times 10^8$ photons/sec, 95% CI=$1.6 \times 10^8$ to $1.2 \times 10^9$ photons/sec; P=0.017, FIG. 5D) and lung metastasis (control, mean=$5.9 \times 10^7$ versus cromolyn, mean=$3.2 \times 10^6$ photons/sec, difference=$5.6 \times 10^7$ photons/sec, 95% CI=$1.5 \times 10^7$ to $9.7 \times 10^7$ photons/sec; P=0.013, FIG. 5E) in the MPanc-96 model. In the MPanc-96 model, the combination of gemcitabine with cromolyn was not greater than either drug alone. In the Panc-1 in vivo model, neither cromolyn nor gemcitabine nor the combination reduced liver or lung metastasis (FIGS. 6D and 6E).

Figure 4F:
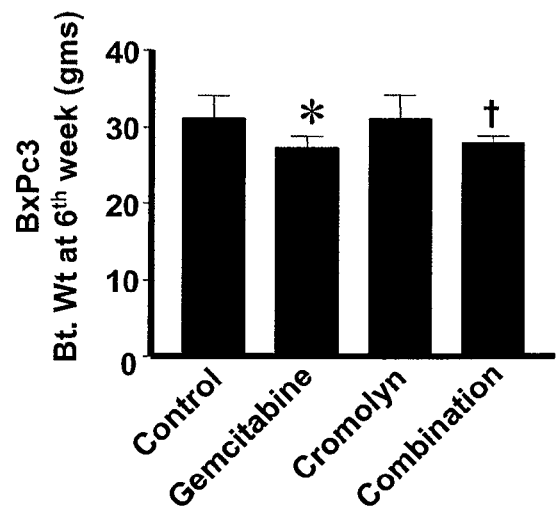
Figure 5F:
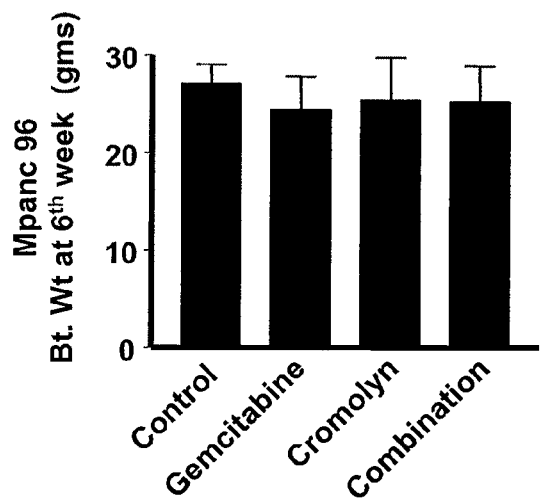
Figure 6F:
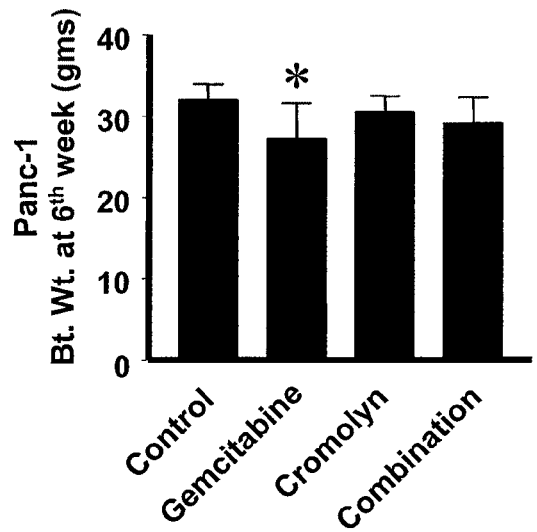

As an indication of overall toxicity, the effects of the treatments on body weight at the end of the experiment were evaluated. Gemcitabine treatment caused a small but statistically significant decrease in body weight in the BxPC-3 (control, mean=31.1 versus gemcitabine, mean=27.2 g, difference=3.9 g, 95% CI=1.0 to 6.7 g; P=0.013, FIG. 4F) and Panc-1 (control, mean=32.0 g versus gemcitabine, mean=27.2 g, difference=4.8 g, 95% CI=0.82 g to 8.7 g; P=0.024, FIG. 6F) tumor models. However, daily injections of cromolyn had no effect on body weight for up to 6 weeks in any of the three models (FIGS. 4F, 5F, and 6, F). The combination of cromolyn with gemcitabine reduced body weight in the BxPC-3 cell model, but this effect was not greater than the effect of gemcitabine alone (FIG. 4F). The combination of cromolyn and gemcitabine did not affect body weight in either the MPanc-96 or Panc-1 models (FIGS. 5F and 6F).

Statistical Analysis

Data presented are the means and 95% confidence intervals (CIs) of the three or more independent experiments. For in vitro experiments and in vivo studies on tumor growth, comparisons between groups were made using a two-tailed two-sample (unpaired) Student's t-test. For the in vivo experiments of NFκB activity, a two-tailed (paired) Student's t-test was used. Differences for which P<0.05 were considered statistically significant.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Examples Relating to Cromolyn and C5

With respect to FIGS. 7-12, cromolyn and its analogues were synthesized on the basis of a procedure described by Cairns et al., J Med. Chem. 1972 June; 15(6):583-9. Bis(o-hydroxyacetophenone) was formed from a condensation reaction between 2,6-dihydroxyacetophenone and dibromoalkane using $K_2CO_3$ in acetone. The bis(o-hydroxyacetophenone) was then condensed with an excess of diethyl oxalate and the resultant bis(2,4-dioxobutyric acid) esters were cyclized under acid conditions. Finally, the diesters were converted to the corresponding disodium salts by a saponification reaction with 20% $NaHCO_3$ solution. (Scheme-1).

Scheme-1: Reagents and conditions (i) $(CH_2)_nBr_2$, $K_2CO_3$, acetone, reflux 24 h; (ii) NaOEt, EtOH, $(COOEt)_2$, 16 h, EtOH, HCl 5 min; (iii) $NaHCO_3$ (20%) in water, 80° C., 3 h.

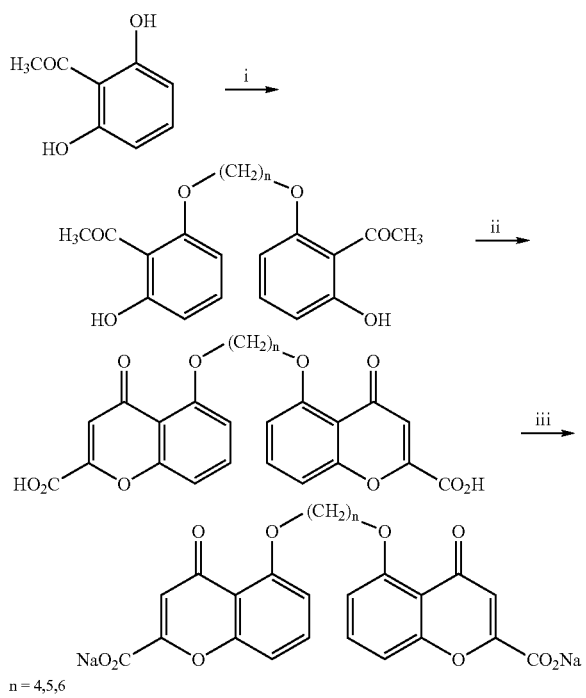

n = 4,5,6

Furthermore, with respect to FIGS. 7-12, all chemicals and solvents were obtained from Sigma-Aldrich (Milwaukee, Wis.) of Fisher Scientific (Pittsburgh, Pa.) and used without further purification. Melting points were measured in open capillary tubes on a BuchiMelting Point B-545 apparatus and were uncorrected. H-NMR and C-NMR spectra were recorded on an IBM-BruckerAvance600 (600 MHz for H-NMR and 150.90 MHz for C-NMR) spectrometers. Chemical shifts (δ) were determined relative to DMSO-d (referenced to 2.49 ppm (δ) for H-NMR and 39.5 ppm for C-NMR). Proton-proton coupling constants (J) were given in Hertz and spectral splitting patterns were designated as singlet (s), doublet (d), triplet (t), quadruplet (q), multipletor overlapped (m), and broad (br). Low resolution mass spectra (ionspray, a variation of electrospray) were acquired on a Perkin-Elmer SciexAPI 100 spectrometer or Applied BiosystemsQ-rap 2000 LC-MS-MS. Flash chromatography was performed using Merksilica gel 60 (mesh size 230-400 ASTM) or using an Isco (Lincon, Nebr.) combiFlashCompanion or SQ16x flash chromatography system with RediSep columns (normal phase silica gel (mesh size 230-400ASTM) and Fisher Optima TM grade solvents. Thin-layer chromatography (TLC) was performed on E. Merk (Darmstadt, Germany) silica gel F-254 aluminum-backed plates with visualization under UV (254 nm) and by staining with potassium permanganate or cericammonium molybdate.

Figure 7:
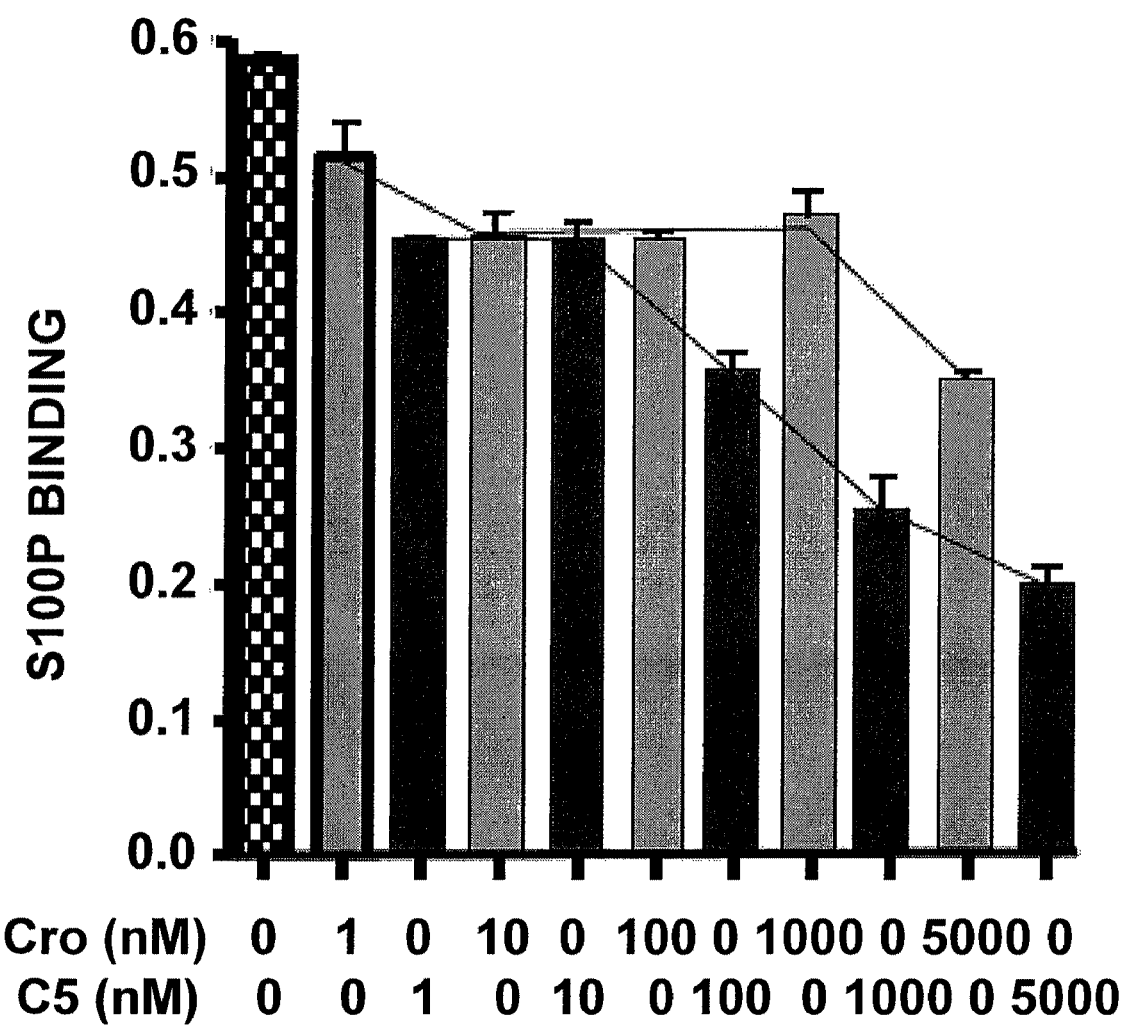
FIG. 7 shows the effect of cromolyn and C5 on S100P binding with RAGE. sRAGE (extracellular portion of RAGE) was coated on an ELISA plate and S100P was added and incubated to allow the binding between S100P and RAGE. After removing un-bound S100P by washing with detergent, the bound S100P and RAGE complex was quantified by adding HRP labeled antibody against S100P. *, P=0.04 C5 μM versus cromolyn 5 μM. Two-tailed two-sample (unpaired) Student's t-tests were used to determine P values.

As can be seen in FIG. 7, the interaction between S100P with RAGE was blocked both by cromolyn and C5, but C5 was more potent than cromolyn. Furthermore, C5 achieved the same level of S100P inhibition at 100 nM as cromolyn achieved at 5000 nM.

Figure 8:
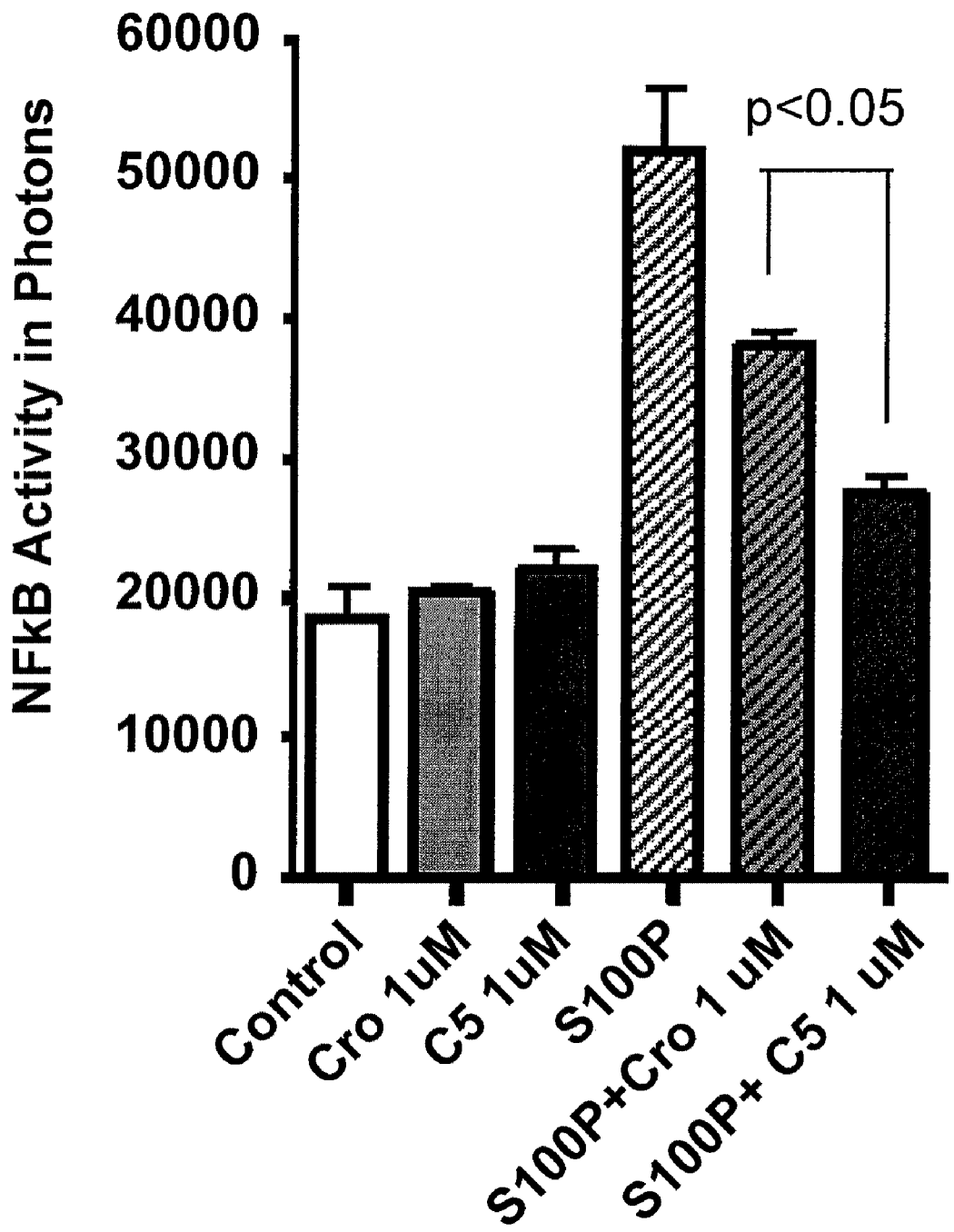
FIG. 8 shows the effect of cromolyn and C5 on S100P stimulated NFκB activity in pancreatic cancer cells in vitro. MPanc-96 pancreatic cancer cell lines stably expressing an NFκB luciferase reporter were examined for the effects of S100P, cromolyn and C5. Cells were plated at $5.0 \times 10^3$ cells/well, treated for 5 hours with 100 nM of S100P, with or without cromolyn and C5 (1 μM), and activity of a luciferase gene driven by the NFκB promoter was analyzed. P=0.05 C5 versus cromolyn. Two-tailed two-sample (unpaired) Student's t-tests were used to determine P values.

As can be seen in FIG. 8, C5 and cromolyn inhibit NFκB activity in pancreatic cancer cells in vitro. Furthermore, C5 reduced S100P induced NFκB activity much better than cromolyn at the same dose.

Figure 9:
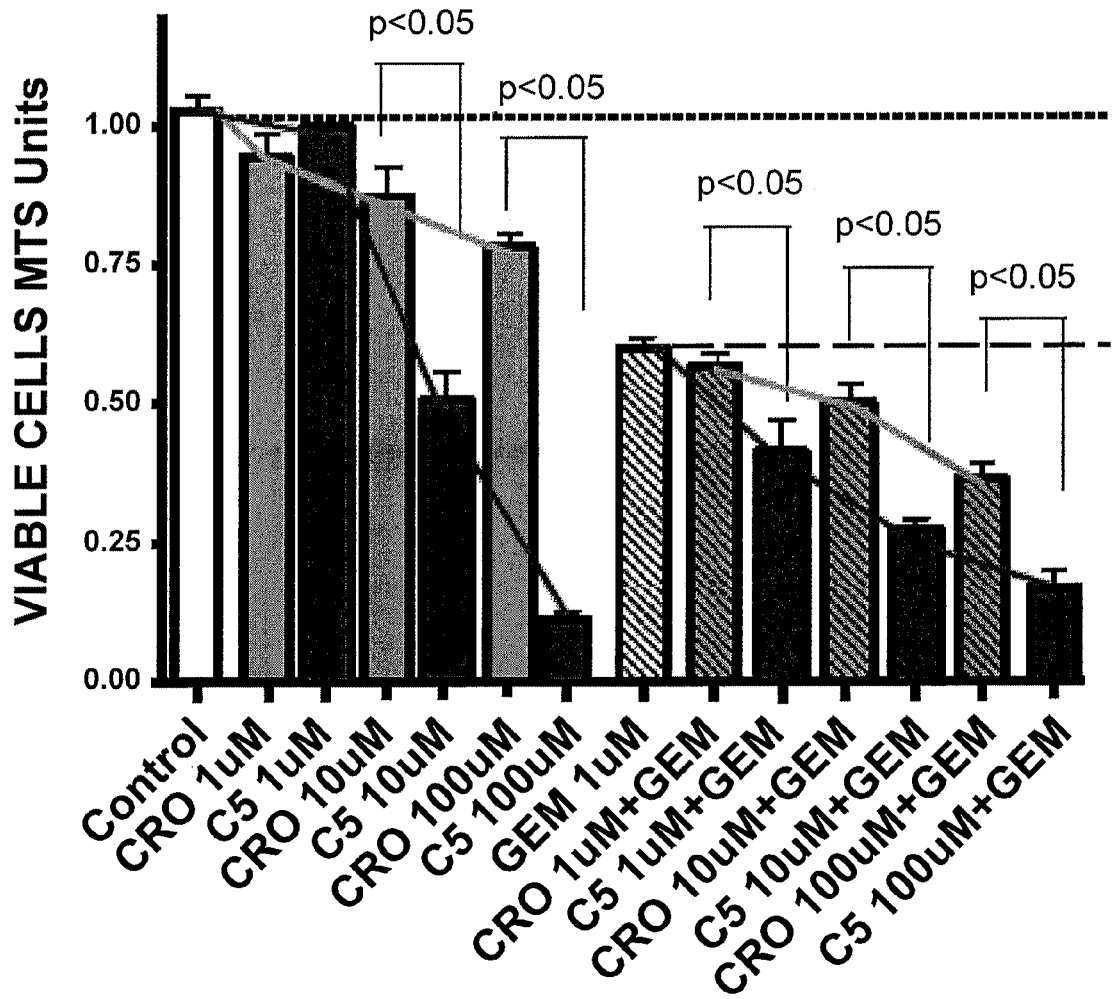
FIG. 9 shows the effect of cromolyn alone, C5 alone or each in combination with gemcitabine on BxPC-3 cell viability. BxPC-3 cells were plated at $1.0 \times 10^3$ cells/well and treated with 0 μM, 1 μM, 10 μM, and 100 μM of cromolyn or C5 alone or in combination with gemcitabine 1 μM and cell viability was analyzed after 72 hours. Two-tailed two-sample (unpaired) Student's t-tests were used to determine P values.
Figure 10:
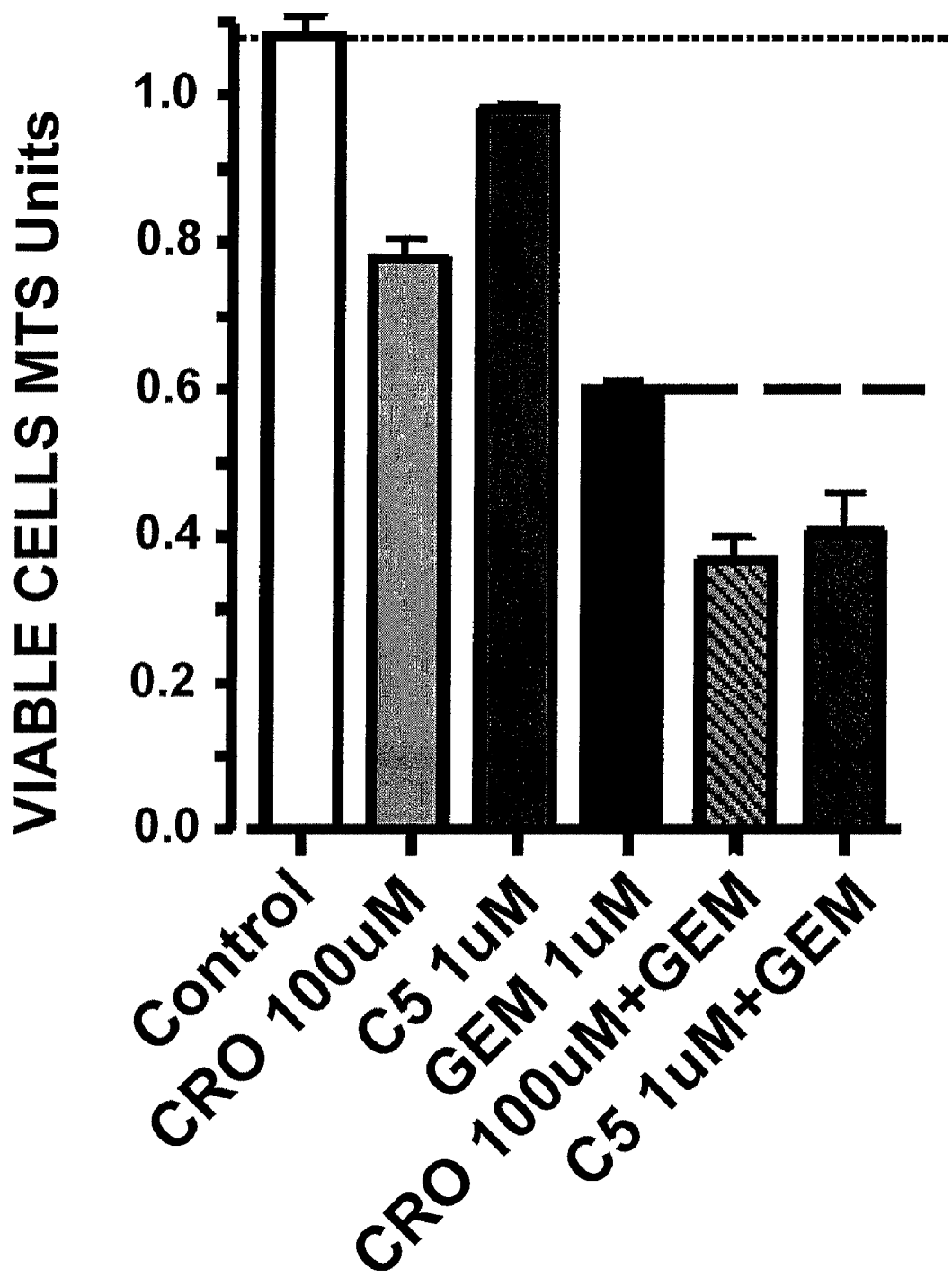
FIG. 10 shows the efficacy of C5 versus cromolyn on BxPC-3 cell viability. BxPC-3 cells were plated at $1.0 \times 10^3$ cells/well and treated with either 100 μM of cromolyn or 1 μM C5 alone or in combination with gemcitabine (1 μM) and cell viability was analyzed after 72 hours.

As can be seen in FIGS. 9 and 10, C5 and cromolyn, alone and in conjunction with gemcitabine, inhibit BxPC-3 cell viability. C5 alone had a dose-dependent effect on blocking cell growth and this effect was more potent and more efficacious than cromolyn at either 10 or 100 μM, P=0.05. C5 was also more potent and efficacious at inhibiting BxPC-3 cell viability in combination with gemcitabine than was cromolyn at all doses investigated (1-100 μM, P=0.05). As seen in FIG. 10, the same level of cell reduction observed with cromolyn at 100 μM in combination with gemcitabine was achieved with 1 μM concentration of C5.

Figure 11:
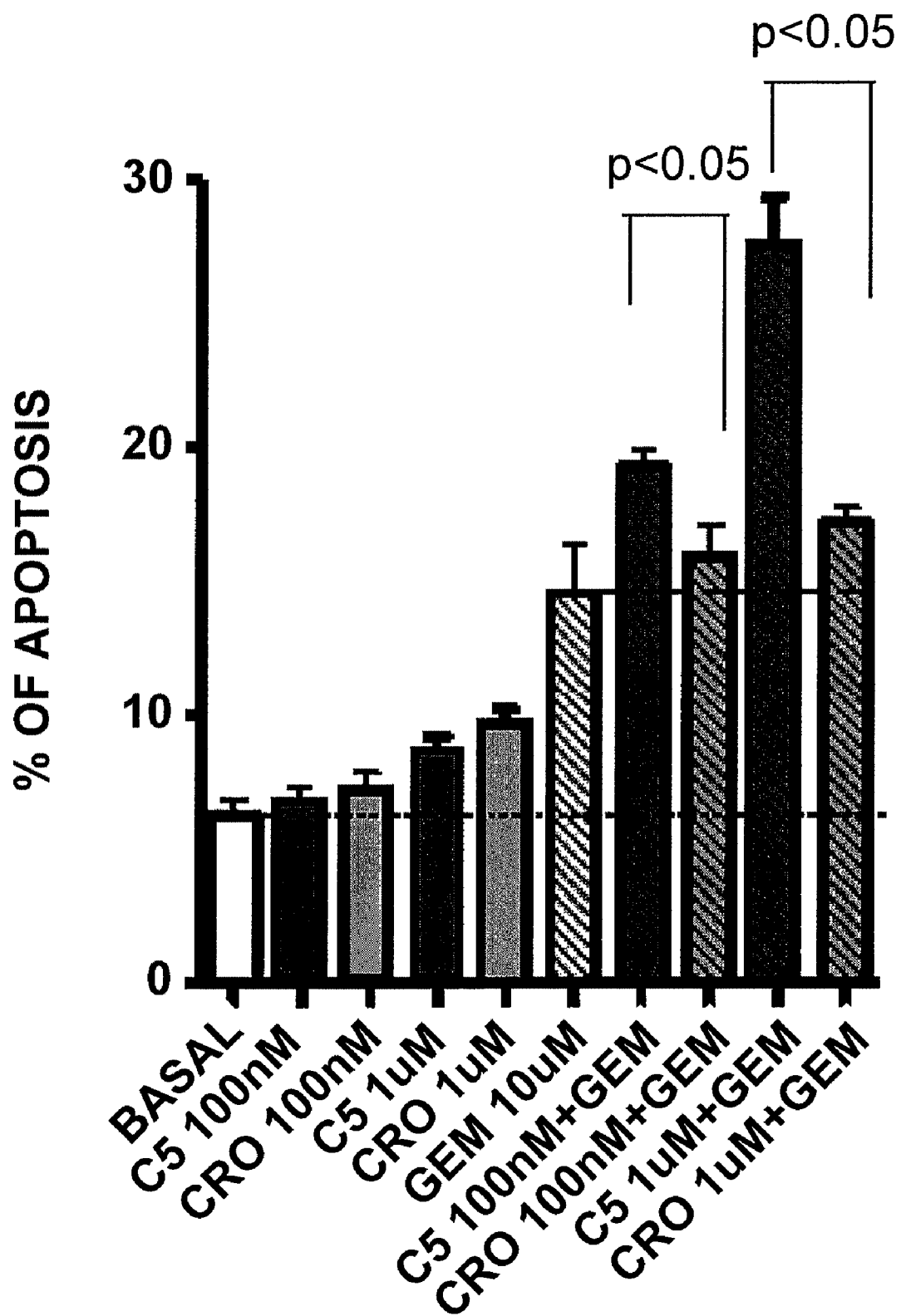
FIG. 11 compares the effects of cromolyn and C5 alone and in combination with gemcitabine on MPanc-96 cell apoptosis. MPanc-96 cells were treated with cromolyn or C5 (100 and 1000 nM) with (+) or without (−) gemcitabine (10 μM). Apoptosis was analyzed after 72 hours by flow cytometry.

As can be seen in FIG. 11, C5 and cromolyn, alone and in conjunction with gemcitabine, inhibit MPanc-96 cell viability. C5 in combination with gemcitabine induced more apoptosis than cromolyn in combination with gemcitabine at both doses investigated *, P<0.05. Two-tailed two-sample (unpaired) Student's t-tests were used to determine P values.

Figure 12:
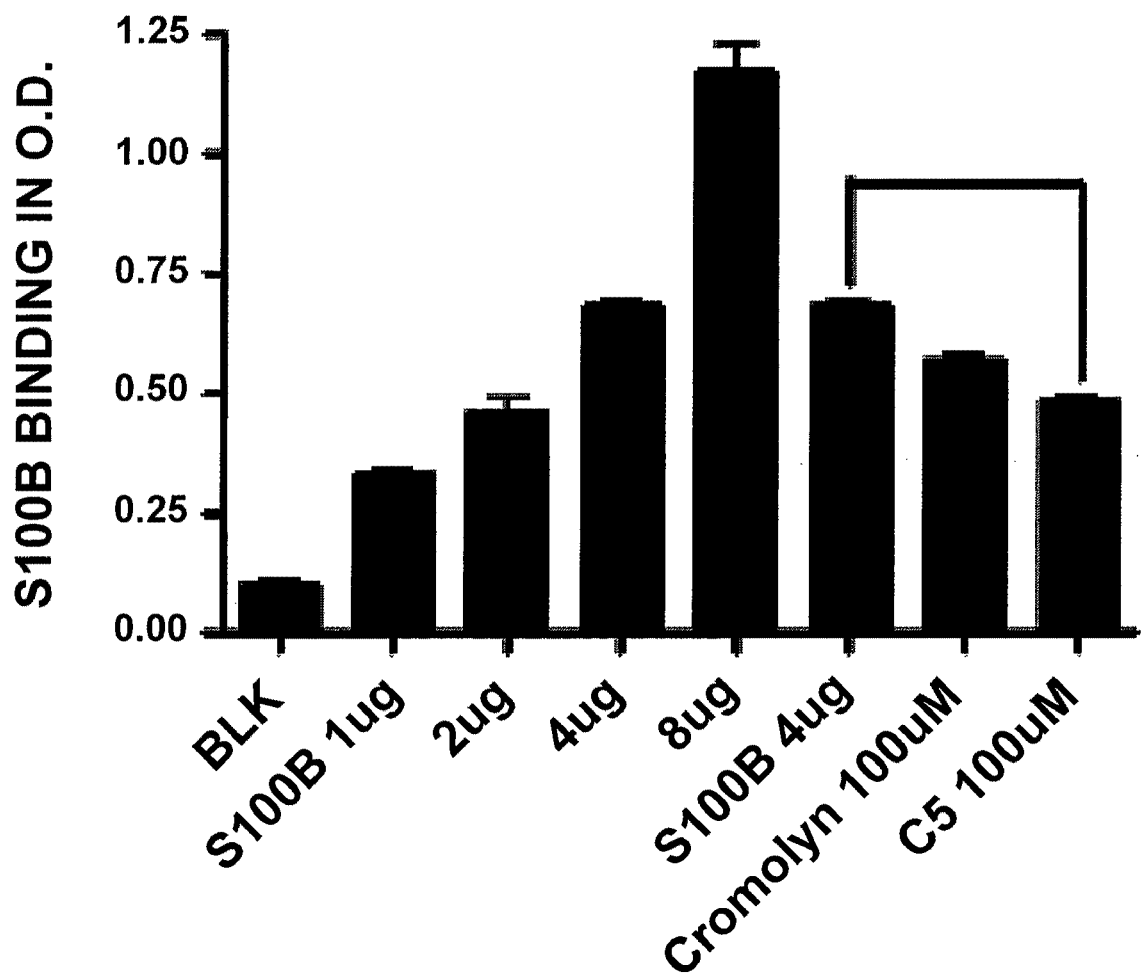
FIG. 12 shows the effect of cromolyn and C5 on the interaction of S100B with RAGE. sRAGE (extracellular portion of RAGE) was coated on an ELISA plate and S100B was added and incubated to allow the binding between S100B and RAGE. After removing un-bound S100B by washing with detergent, bound S100B and RAGE complex was quantified by adding HRP labeled antibody against S100B.

As can be seen in FIG. 12, C5 and cromolyn inhibit the interaction of S100B with RAGE.

Figure 13:
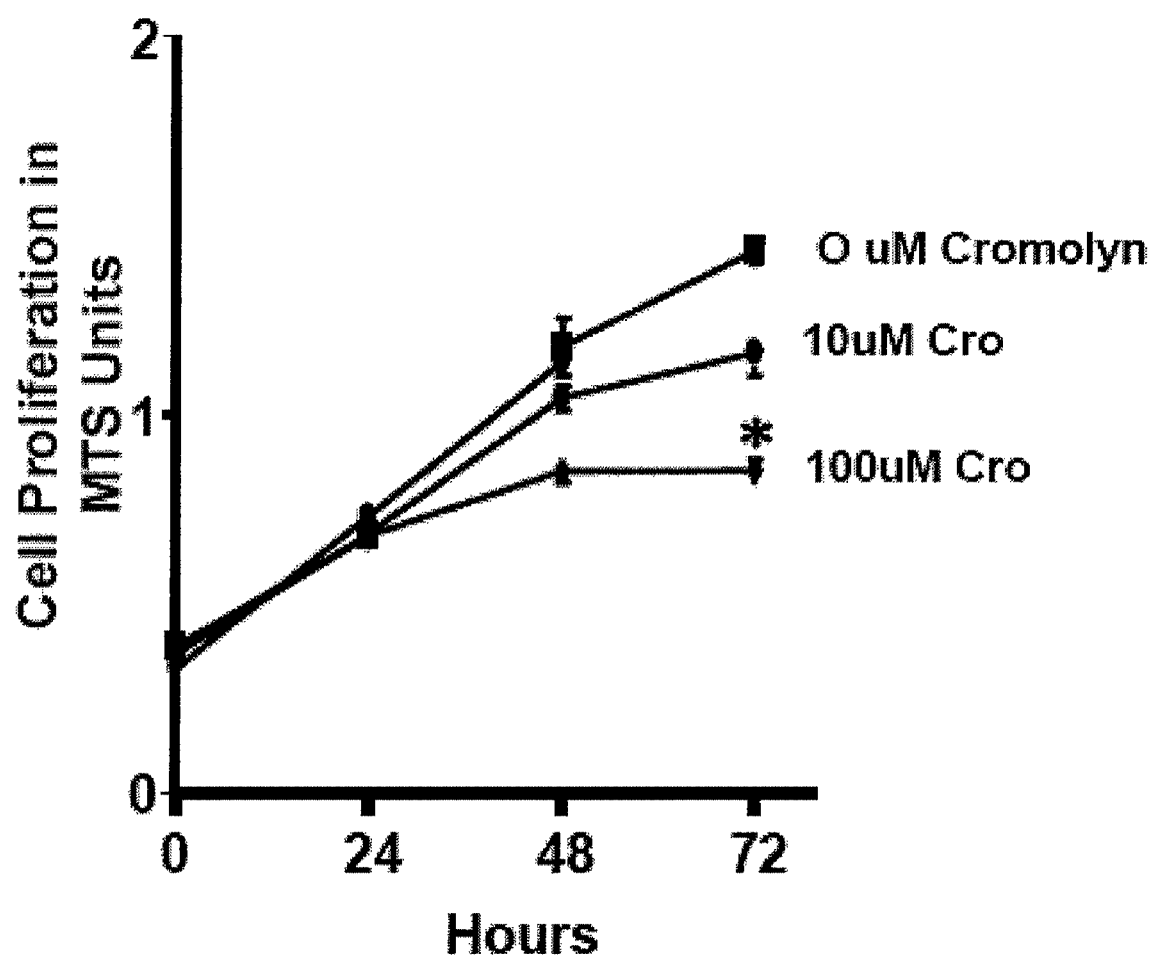
FIG. 13 shows the effect of cromolyn on cell proliferation. SKOV3 ovarian cells were cultured for up to three days in the presence of different concentrations of cromolyn, and cell proliferation was analyzed at 24, 48, and 72 hours. *, P<0.05.

As can be seen in FIG. 13, cromolyn reduced the growth of the ovarian cell line SKOV3.

Figure 14:
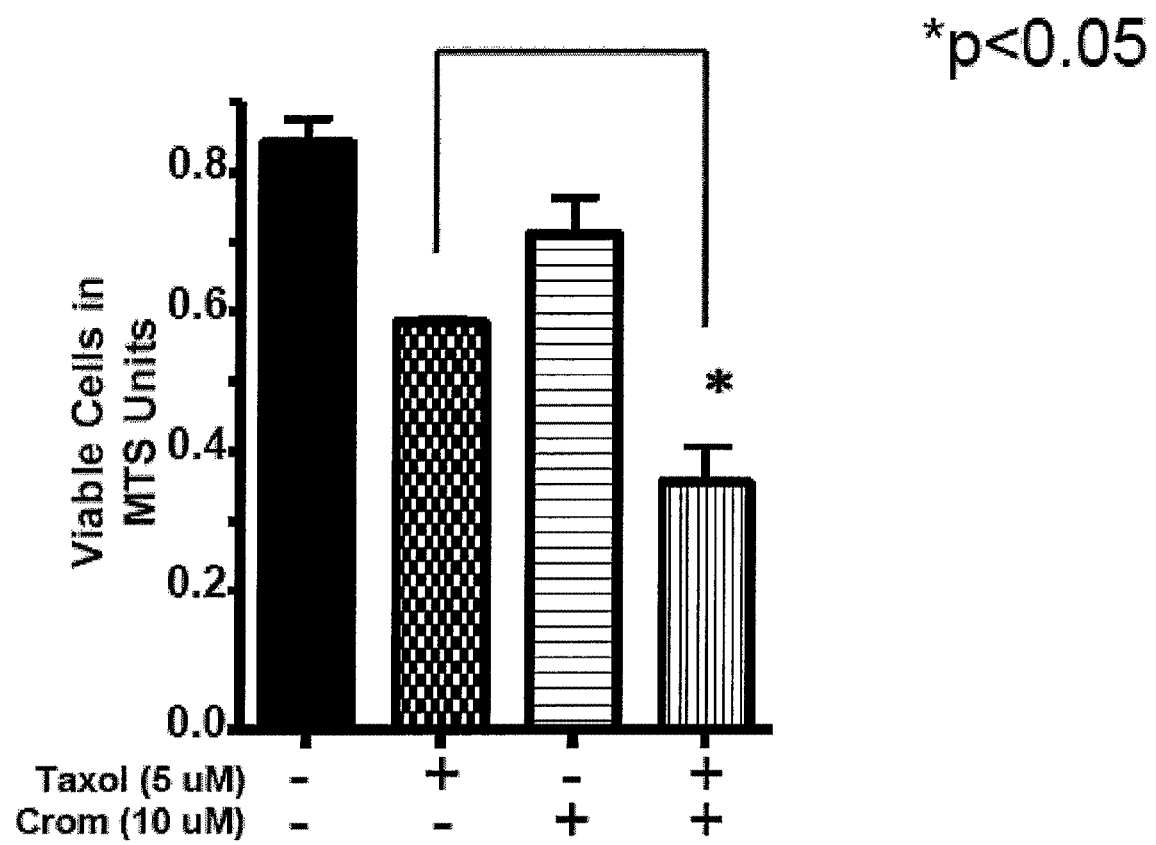
FIG. 14 shows the effect of cromolyn alone, taxol alone or cromolyn and taxol in combination on SKOV3 ovarian cell viability. SKOV3 ovarian cells were plated and treated with taxol (5 μM) either in the presence or absence of cromolyn (10 μM) for 48 hours. Cell viability was analyzed after 48 hours. *, P<0.05.

As can be seen in FIG. 14, cromolyn increased the cell killing effect of taxol on ovarian cancer cells.

Figure 15:
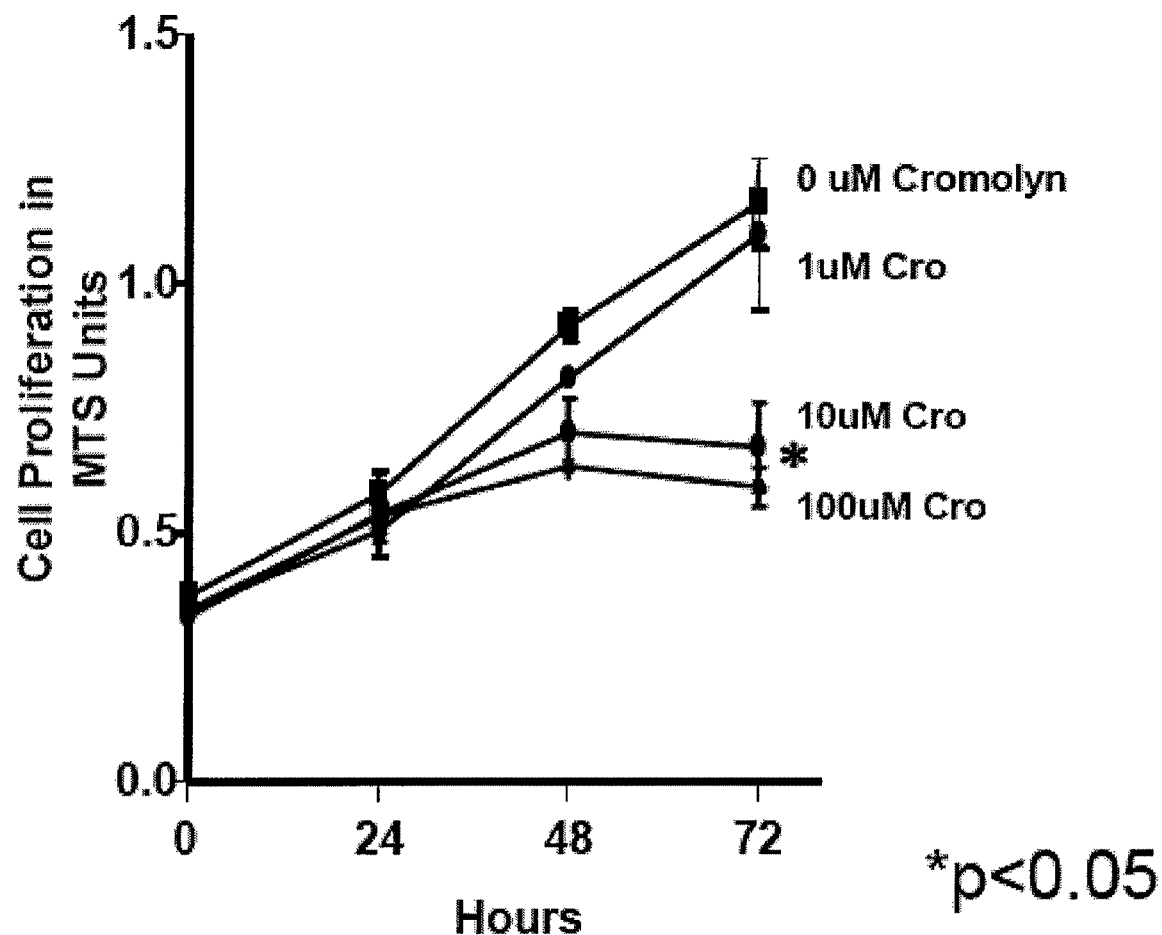
FIG. 15 shows the effect of cromolyn on cell proliferation. PC3 prostate cells were cultured for up to three days in the presence of different concentrations of cromolyn, and cell proliferation was analyzed at 24, 48, and 72 hours. *, P<0.05.

As can be seen in FIG. 15, cromolyn reduced growth of the prostate cancer cell line PC3.

Figure 16:
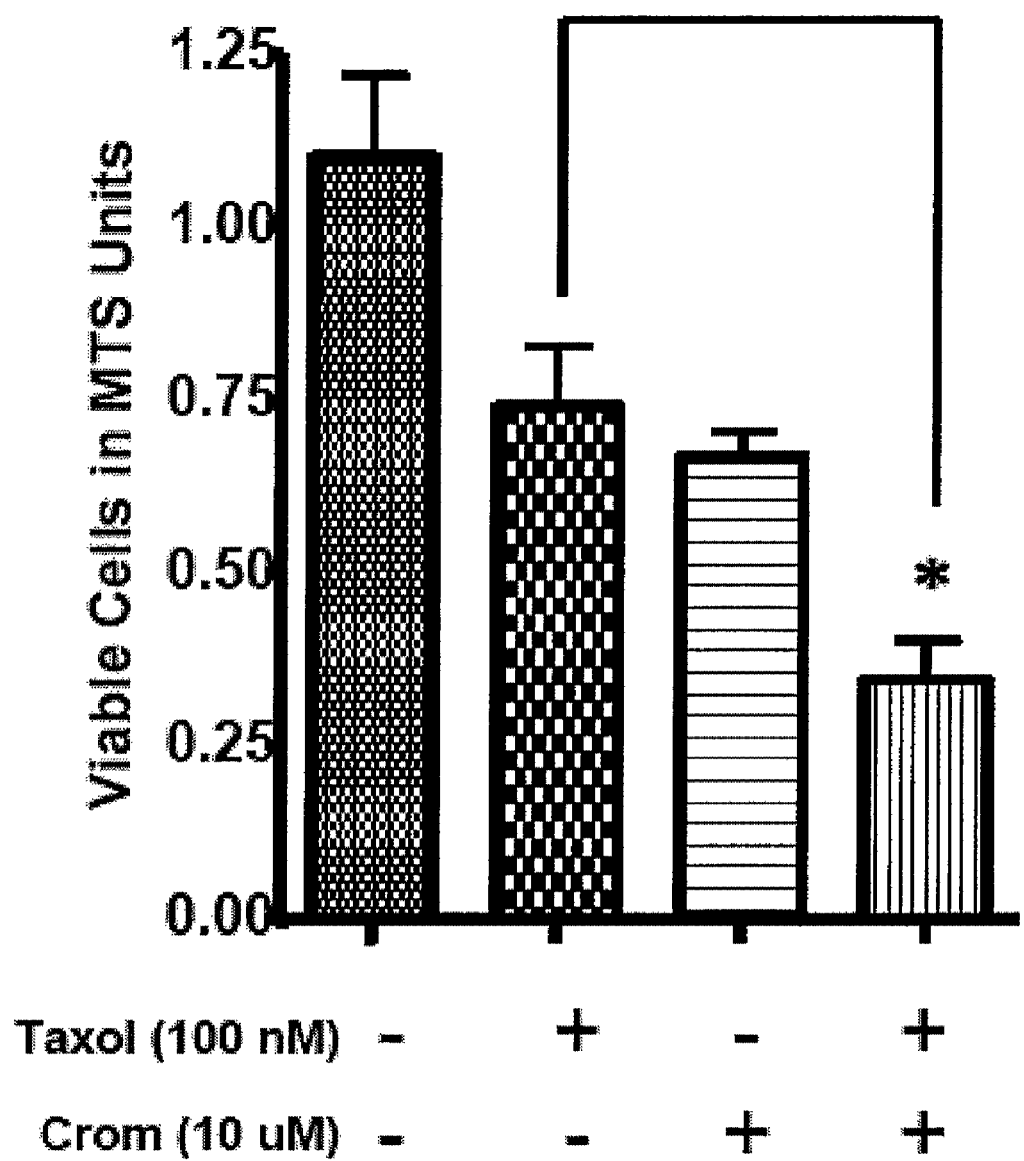
FIG. 16 shows the effect of cromolyn alone, taxol alone or cromolyn and taxol in combination on PC3 prostate cell viability. PC3 prostate cells were plated and treated with taxol (100 nM) either in the presence or absence of cromolyn (10 μM) for 48 hours. Cell viability was analyzed after 48 hours. *, P<0.05.

As can be seen in FIG. 16, cromolyn increased the cell killing effect of taxol on prostate cancer cells.

Figure 17:
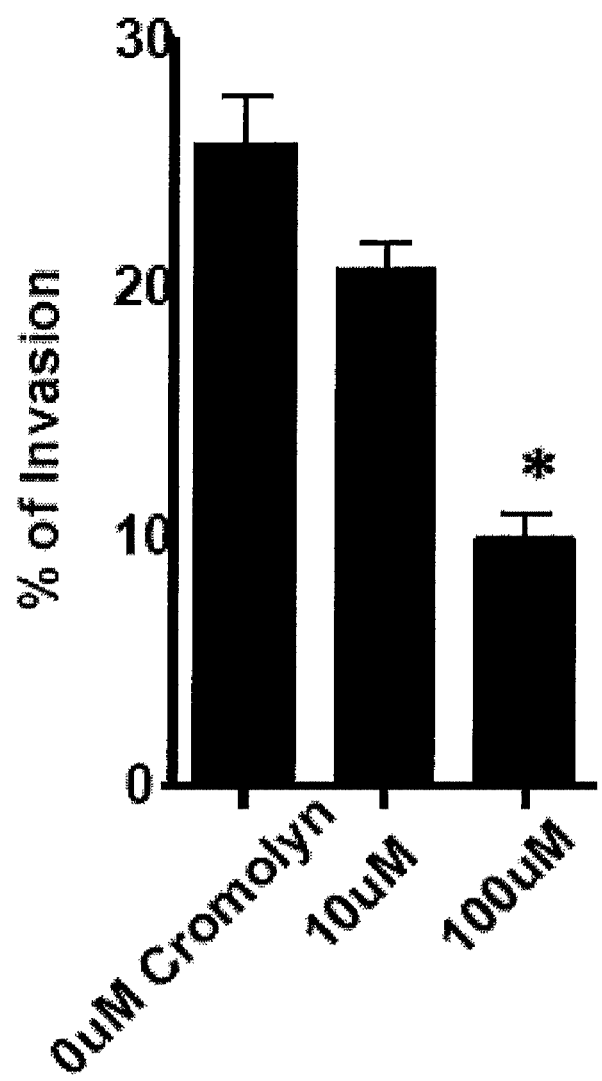
FIG. 17 shows the effect of cromolyn on colon cancer cell invasion. SW480 cells were plated on top of a layer of matrigel in a Boyden type chamber (transwell). Media containing 5% FBS was placed in the lower well and the cells were allowed to invade the matrigel layer for 24 hours in the presence of different concentrations of cromolyn.

As can be seen in FIG. 17, cromolyn reduced the invasiveness of the colon cancer cell line SW480.

Figure 18:
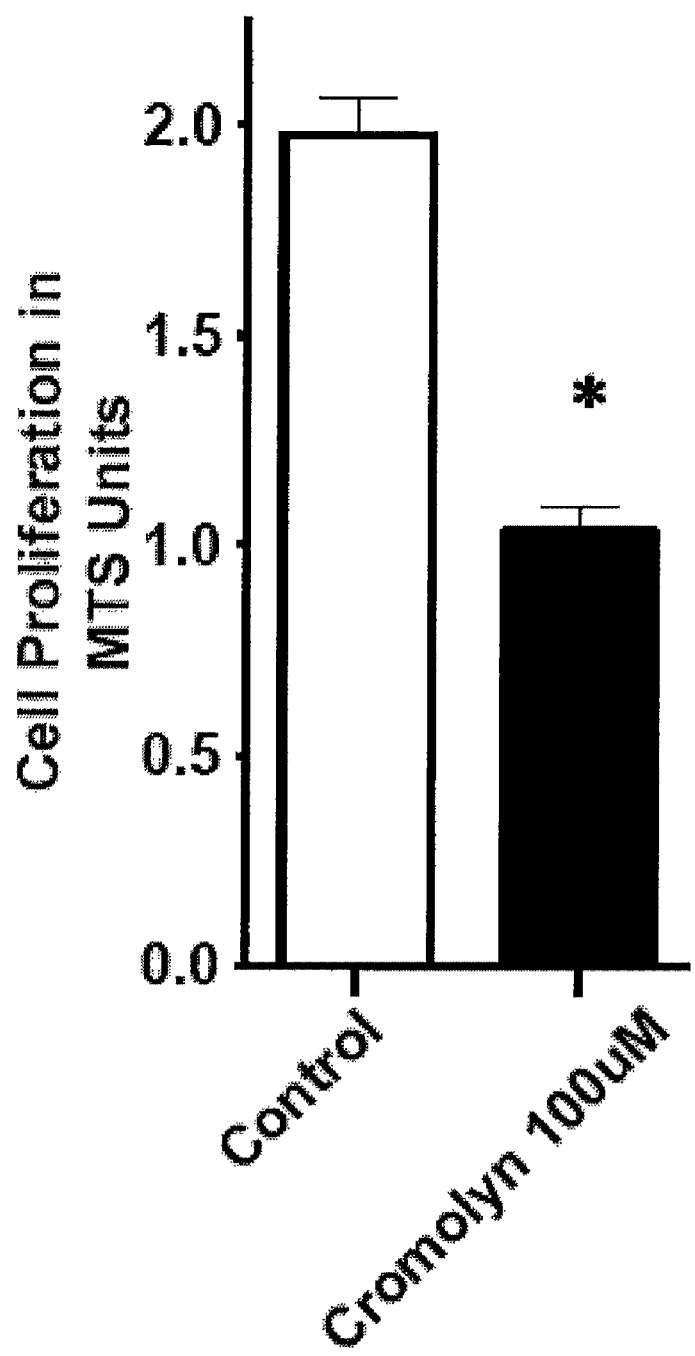
FIG. 18 shows the effect of cromolyn on cell proliferation. SW480 colon cells were cultured for up to three days in the presence of cromolyn (100 μM), and cell proliferation was analyzed. *, P<0.05.

As can be seen in FIG. 18, cromolyn reduced growth of the colon cancer SW480 cell line.

Cell Lysate Array Analysis
Detection and Imaging of Cell Lysis Array:
Detection of S100P was done by a modified DAKO CSA kit (DakoCytomation, Carpinteria, Calif.) catalog #K1500. Briefly, the slides were blocked with reblot+Mild (Chemicon, Temecula, Calif.) catalog #2502, followed by overnight blocking with i-block (Applied Biosystems, Foster City, Calif.) catalog #Tropix A1300. The next day, blocking continued with fresh 3% hydrogen peroxide, avidin/Biotin and casein block. Primary antibody S100P (Cat. No: AF2957; R&D Systems, Minn.) was diluted in antibody dilution buffer and incubated at 25° C. for 1 h in a humid chamber. Secondary biotinylated antibody (Vector Laboratories, Burlingame, Calif.) were diluted 1:10000 and incubated as before. Final steps included streptavidin-biotin, amplification reagent and streptavidin/peroxidase incubations from the CSA kit followed by DAB+development. TBS-T washes preceded all steps for the removal for the previous reagent. Slides were scanned in color at 1200 DPI; the resulting image was converted to a 16-bit grayscale and inverted (negative) to allow quantification by ArrayVision™ (Imaging Research Inc.).

| Cancer Cell Lines Type | Percentage of Cell Lines Positive for S100P |
|---|---|
| Pancreatic | 100 (9/9) |
| Colon | 50 (4/8) |
| Glioma | 0 (0/8) |
| Leaukemia | 33 (2/6) |
| Lung | 46 (6/13) |
| Melanoma | 50 (2/4) |
| Ovarian | 100 (5/5) |
| Breast | 21 (3/14) |
| Prostate | 83 (5/6) |
| Sarcoma | 7 (1/14) |

REFERENCES

1. Jemal A, Murray T, Samuels A, Ghafoor A, Ward E, Thun M J. Cancer statistics, 2003. CA Cancer J Clin 2003 January; 53(1):5-26.
2. Maheshwari V, Moser A J. Current management of locally advanced pancreatic cancer. Nat Clin Pract Gastroenterol Hepatol 2005 August; 2(8):356-64.
3. Ko A H, Tempero M A. Treatment of metastatic pancreatic cancer. J Natl Compr Canc Netw 2005 September; 3(5): 627-36.
4. Moore M J, Hamm J, Dancey J, Eisenberg P D, Dagenais M, Fields A, et al. Comparison of gemcitabine versus the matrix metalloproteinase inhibitor BAY 12-9566 in patients with advanced or metastatic adenocarcinoma of the pancreas: a phase III trial of the National Cancer Institute of Canada Clinical Trials Group. J Clin Oncol 2003 Sep. 1; 21(17):3296-302.
5. Logsdon C D, Simeone D M, Binkley C, Arumugam T, Greenson J K, Giordano T J, et al. Molecular profiling of pancreatic adenocarcinoma and chronic pancreatitis identifies multiple genes differentially regulated in pancreatic cancer. Cancer Res 2003 May 15; 63(10):2649-57.
6. Crnogorac-Jurcevic T, Missiaglia E, Blayeri E, Gangeswaran R, Jones M, Terris B, et al. Molecular alterations in pancreatic carcinoma: expression profiling shows that dysregulated expression of S100 genes is highly prevalent. J Pathol 2003 September; 201(1):63-74.
7. Sato N, Fukushima N, Matsubayashi H, Goggins M. Identification of maspin and S100P as novel hypomethylation targets in pancreatic cancer using global gene expression profiling. Oncogene 2004 Feb. 26; 23(8): 1531-8.
8. Wang G Z, Platt-Higgins A, Carroll J, Rudland S D, Winstanley J, Barraclough R, et al. Induction of metastasis by S100P in a rat mammary model and its association with poor survival of breast cancer patients. Cancer Research 2006 Jan. 15; 66(2):1199-207.
9. Beer D G, Kardia S L, Huang C C, Giordano T J, Levin A M, Misek D E, et al. Gene-expression profiles predict survival of patients with lung adenocarcinoma. Nat Med 2002 August; 8(8):816-24.
10. Becker T, Gerke V, Kube E, Weber K. S100P, a novel Ca(2+)-binding protein from human placenta. cDNA cloning, recombinant protein expression and Ca2+ binding properties. Eur J Biochem 1992 Jul. 15; 207(2):541-7.
11. Arumugam T, Simeone D M, Van Golen K, Logsdon C D. S100P promotes pancreatic cancer growth, survival, and invasion. Clin Cancer Res 2005 Aug. 1; 11(15):5356-64.
12. Bertram J, Palfner K, Hiddemann W, Kneba M. Elevated expression of S100P, CAPL and MAGE 3 in doxorubicin-resistant cell lines: comparison of mRNA differential display reverse transcription-polymerase chain reaction and subtractive suppressive hybridization for the analysis of differential gene expression. Anticancer Drugs 1998 April; 9(4):311-7.
13. Arumugam T, Simeone D M, Schmidt A M, Logsdon C D. S100P stimulates cell proliferation and survival via receptor for activated glycation end products (RAGE). J Biol Chem 2004 Feb. 13; 279(7):5059-65.
14. Stem D, Du Y S, Fang Y S, Marie S A. Receptor for advanced glycation endproducts: a multiligand receptor magnifying cell stress in diverse pathologic settings. Adv Drug Deliv Rev 2002 Dec. 7; 54(12):1615-25.
15. Wang W, Abbruzzese J L, Evans D B, Larry L, Cleary K R, Chiao P J. The nuclear factor-kappa B RelA transcription factor is constitutively activated in human pancreatic adenocarcinoma cells. Clin Cancer Res 1999 January; 5(1): 119-27.
16. Karin M, Cao Y, Greten F R, Li Z W. NF-kappaB in cancer: from innocent bystander to major culprit. Nat Rev Cancer 2002 April; 2(4):301-10.
17. Arlt A, Vorndamm J, Breitenbroich M, Folsch U R, Kalthoff H, Schmidt W E, et al. Inhibition of NF-kappaB sensitizes human pancreatic carcinoma cells to apoptosis induced by etoposide (VP16) or doxorubicin. Oncogene 2001 Feb. 15; 20(7):859-68.
18. Storms W, Kaliner M A. Cromolyn sodium: fitting an old friend into current asthma treatment. J Asthma 2005 March; 42(2):79-89.
19. Oyama Y, Shishibori T, Yamashita K, Naya T, Nakagiri S, Maeta H, et al. Two distinct anti-allergic drugs, amlexanox and cromolyn, bind to the same kinds of calcium binding proteins, except calmodulin, in bovine lung extract. Biochem Biophys Res Commun 1997 Nov. 17; 240(2):341-7.
20. Okada M, Tokumitsu H, Kubota Y, Kobayashi R. Interaction of S100 proteins with the antiallergic drugs, olopatadine, amlexanox, and cromolyn: Identification of putative drug binding sites on S100A1 protein. Biochem Biophys Res Commun 2002 Apr. 12; 292(4):1023-30.
21. Shishibori T, Oyama Y, Matsushita O, Yamashita K, Furuichi H, Okabe A, et al. Three distinct anti-allergic drugs, amlexanox, cromolyn and tranilast, bind to S100A12 and S100A13 of the S100 protein family. Biochem J 1999 Mar. 15; 338 (Pt 3):583-9.
22. Peiper M, Nagoshi M, Patel D, Fletcher J A, Goegebuure P S, Eberlein T J. Human pancreatic cancer cells (MPanc-96) recognized by autologous tumor-infiltrating lymphocytes after in vitro as well as in vivo tumor expansion. Int J Cancer 1997 Jun. 11; 71(6):993-9.
23. Qin X F, An D S, Chen I S, Baltimore D. Inhibiting HIV-1 infection in human T cells by lentiviral-mediated delivery of small interfering RNA against CCR5. Proc Natl Acad Sci USA 2003 Jan. 7; 100(1):183-8.
24. Mazurek N, Schindler H, Schurholz T, Pecht I. The cromolyn binding protein constitutes the Ca2+ channel of basophils opening upon immunological stimulus. Proc Natl Acad Sci USA 1984 November; 81(21):6841-5.
25. Cox A, Law N M, Findlay J B. Inhibition of cromolyn-induced phosphorylation of a 78-kDa protein by phorbol esters in rat peritoneal mast cells. Biochem Pharmacol 1998 Mar. 1; 55(5):585-94.
26. Garland L G, Mongar J L. Inhibition by cromoglycate of histamine release from rat peritoneal mast cells induced by mixtures of dextran, phosphatidyl serine and calcium ions. Br J Pharmacol 1974 January; 50(1):137-43.
27. White J R, Pearce F L. Effect of anti-allergic compounds on anaphylactic histamine secretion from rat peritoneal mast cells in the presence and absence of exogenous calcium. Immunology 1982 June; 46(2):361-7.
28. Holian A, Hamilton R, Scheulek R K. Mechanistic aspects of cromolyn sodium action on the alveolar macrophage: inhibition of stimulation by soluble agonists. Agents Actions 1991 July; 33(3-4):318-25.
29. Correia I, Wang L, Pang X, Theoharides T C. Characterization of the 78 kDa mast cell protein phosphorylated by the antiallergic drug cromolyn and homology to moesin. Biochem Pharmacol 1996 Aug. 9; 52(3):413-24.
30. Reinsprecht M, Pecht I, Schindler H, Romanin C. Potent block of Cl— channels by antiallergic drugs. Biochem Biophys Res Commun 1992 Nov. 16; 188(3):957-63.

31. Lucas A M, Shuster S. Cromolyn inhibition of protein kinase C activity. Biochem Pharmacol 1987 Feb. 15; 36(4): 562-5.
32. Hemmerich S, Yarden Y, Pecht I. A cromoglycate binding protein from rat mast cells of a leukemia line is a nucleoside diphosphate kinase. Biochemistry 1992 May 19; 31(19):4574-9.
33. Samoszuk M, Corwin M A. Mast cell inhibitor cromolyn increases blood clotting and hypoxia in murine breast cancer. International Journal of Cancer 2003 Oct. 20; 107(1): 159-63.
34. Ionov I D. Inhibition of Mast-Cell Activity As A New Approach to Anticancer Therapy. International Journal of Radiation Biology 1991 July; 60(1-2):287-91.
35. Donato R. Intracellular and extracellular roles of S100 proteins. Microsc Res Tech 2003 Apr. 15; 60(6):540-51.
36. Averboukh L, Liang P, Kantoff P W, Pardee A B. Regulation of S100P expression by androgen. Prostate 1996 December; 29(6):350-5.
37. Crnogorac-Jurcevic T, Efthimiou E, Nielsen T, Loader J, Terris B, Stamp G, et al. Expression profiling of microdissected pancreatic adenocarcinomas. Oncogene 2002 Jul. 4; 21(29):4587-94.
38. Cairns H, Fitzmaurice C, Hunter D, Johnson P B, King J, Lee T B, Lord G H, Minshull R, Cox J S., Synthesis and structure-activity relationships of disodium cromoglycate and some related compounds. J Med. Chem. 1972 June; 15(6):583-9.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

What is claimed is:

1. A method of treating a cancer comprising the step of administering to a mammal a therapeutically effective amount of a compound represented by the following Formula (II) or salt thereof:

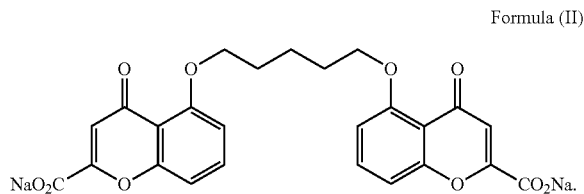

Formula (II)

2. The method of claim 1 further comprising the step of administering to the mammal a therapeutically effective amount of gemcitabine.

3. The method of claim 1 wherein the cancer is pancreatic cancer.

4. The method of claim 1 wherein the mammal is a human.

5. The method of claim 1 wherein the cancer is colon cancer, lung cancer, melanoma, ovarian cancer, breast cancer or prostate cancer.

* * * * *